(12) United States Patent
Chapela et al.

(10) Patent No.: US 10,360,495 B2
(45) Date of Patent: Jul. 23, 2019

(54) AUGMENTED REALITY AND BLOCKCHAIN TECHNOLOGY FOR DECISION AUGMENTATION SYSTEMS AND METHODS USING CONTEXTUAL FILTERING AND PERSONALIZED PROGRAM GENERATION

(71) Applicant: Suggestic, Inc., San Francisco, CA (US)

(72) Inventors: Victor Chapela, Palo Alto, CA (US); Ricardo Corral Corral, Mexico City (MX)

(73) Assignee: Suggestic, Inc., San Francisco, CA (US)

( * ) Notice: Subject to any disclaimer, the term of this patent is extended or adjusted under 35 U.S.C. 154(b) by 0 days.

(21) Appl. No.: 15/859,062

(22) Filed: Dec. 29, 2017

(65) Prior Publication Data
US 2018/0190375 A1     Jul. 5, 2018

Related U.S. Application Data

(60) Provisional application No. 62/440,924, filed on Dec. 30, 2016, provisional application No. 62/440,982, (Continued)

(51) Int. Cl.
*G06T 19/00*     (2011.01)
*A61B 5/00*      (2006.01)
(Continued)

(52) U.S. Cl.
CPC ............ *G06N 3/0427* (2013.01); *A23L 33/40* (2016.08); *A61B 5/0205* (2013.01);
(Continued)

(58) Field of Classification Search
None
See application file for complete search history.

(56) References Cited

U.S. PATENT DOCUMENTS 9,582,913 B1 *   2/2017   Kraft ................. G06T 11/60
2014/0147829 A1 * 5/2014  Jerauld ............... G06F 1/163
                                                434/430
(Continued)

OTHER PUBLICATIONS

Saul B. Needleman et al., "A general method applicable to the search for similarities in the amino acid sequence of two proteins," Journal of Molecular Biology 48, 1970, 8 pages.
(Continued)

*Primary Examiner* — Ryan M Gray
(74) *Attorney, Agent, or Firm* — Carr & Ferrell LLP

(57) ABSTRACT

Augmented reality and blockchain technology for decision augmentation systems and methods using contextual filtering and personalized program generation are provided herein. An example method includes receiving any of an image, a video stream, and contextual data from a mobile device camera, evaluating any of the image, the video stream, and the contextual data for target food or beverage content by determining ingredient and nutritional components of the target food or beverage content, and applying an augmented reality overlay to the target food or beverage content based on the ingredient and nutritional components.

16 Claims, 18 Drawing Sheets

Related U.S. Application Data filed on Dec. 30, 2016, provisional application No. 62/440,689, filed on Dec. 30, 2016, provisional application No. 62/440,801, filed on Dec. 30, 2016, provisional application No. 62/441,043, filed on Dec. 30, 2016, provisional application No. 62/441,014, filed on Dec. 30, 2016.

(51) Int. Cl.

| | | |
|---|---|---|
| *G06F 1/16* | (2006.01) | |
| *G06N 3/02* | (2006.01) | |
| *G06N 3/04* | (2006.01) | |
| *G06N 3/08* | (2006.01) | |
| *G06N 5/04* | (2006.01) | |
| *G09B 5/02* | (2006.01) | |
| *A23L 33/00* | (2016.01) | |
| *A61M 5/142* | (2006.01) | |
| *G06F 16/27* | (2019.01) | |
| *G06N 20/00* | (2019.01) | |
| *G06T 11/20* | (2006.01) | |
| *G06T 11/60* | (2006.01) | |
| *G09B 19/00* | (2006.01) | |
| *G06F 16/901* | (2019.01) | |
| *A61B 5/0205* | (2006.01) | |
| *G16H 20/60* | (2018.01) | |
| *A61B 5/08* | (2006.01) | |
| *A61B 5/021* | (2006.01) | |
| *A61B 5/024* | (2006.01) | |
| *A61B 5/145* | (2006.01) | |
| *A61M 5/172* | (2006.01) | |
| *A61B 5/1455* | (2006.01) | |

(52) U.S. Cl.
CPC ............ *A61B 5/4806* (2013.01); *A61B 5/486* (2013.01); *A61B 5/4866* (2013.01); *A61B 5/681* (2013.01); *A61B 5/6803* (2013.01); *A61M 5/14244* (2013.01); *G06F 1/163* (2013.01); *G06F 16/27* (2019.01); *G06F 16/9024* (2019.01); *G06N 3/02* (2013.01); *G06N 3/08* (2013.01); *G06N 5/045* (2013.01); *G06N 20/00* (2019.01); *G06T 11/206* (2013.01); *G06T 11/60* (2013.01); *G06T 19/006* (2013.01); *G09B 5/02* (2013.01); *G09B 19/00* (2013.01); *G09B 19/0092* (2013.01); *G16H 20/60* (2018.01); *A23V 2002/00* (2013.01); *A61B 5/021* (2013.01); *A61B 5/02438* (2013.01); *A61B 5/08* (2013.01); *A61B 5/14532* (2013.01); *A61B 5/14551* (2013.01); *A61M 5/1723* (2013.01); *A61M 2005/14208* (2013.01)

(56) References Cited

U.S. PATENT DOCUMENTS

| | | | |
|---|---|---|---|
| 2014/0171039 A1* | 6/2014 | Bjontegard | H04W 4/029 455/414.1 |
| 2014/0220516 A1* | 8/2014 | Marshall | G09B 19/0092 434/127 |
| 2018/0158133 A1* | 6/2018 | Davis | G06Q 30/0643 |
| 2018/0189636 A1 | 7/2018 | Chapela et al. | |
| 2018/0190147 A1 | 7/2018 | Chapela et al. | |

OTHER PUBLICATIONS

Temple F. Smith et al., "Identification of Common Molecular Subsequences" Journal of Molecular Biology 147, 1981, 3 pages.
Chapela et al., "Deep Learning Ingredient and Nutrient Identification Systems and Methods", U.S. Appl. No. 15/859,126, filed Dec. 29, 2017, pp. 1-37.
Suppes, P., "A Probabilistic Theory of Causality", Amsterdam: North-Holland Publishing, ISBN0720424046, DOI: 10.1086/288485, 1970, 131 pages.
Cartwright, Nancy, "Causal Laws and Effective Strategies," Noûs, 13(4). DOI:10.2307/2215337, 1979, pp. 419-437.

* cited by examiner

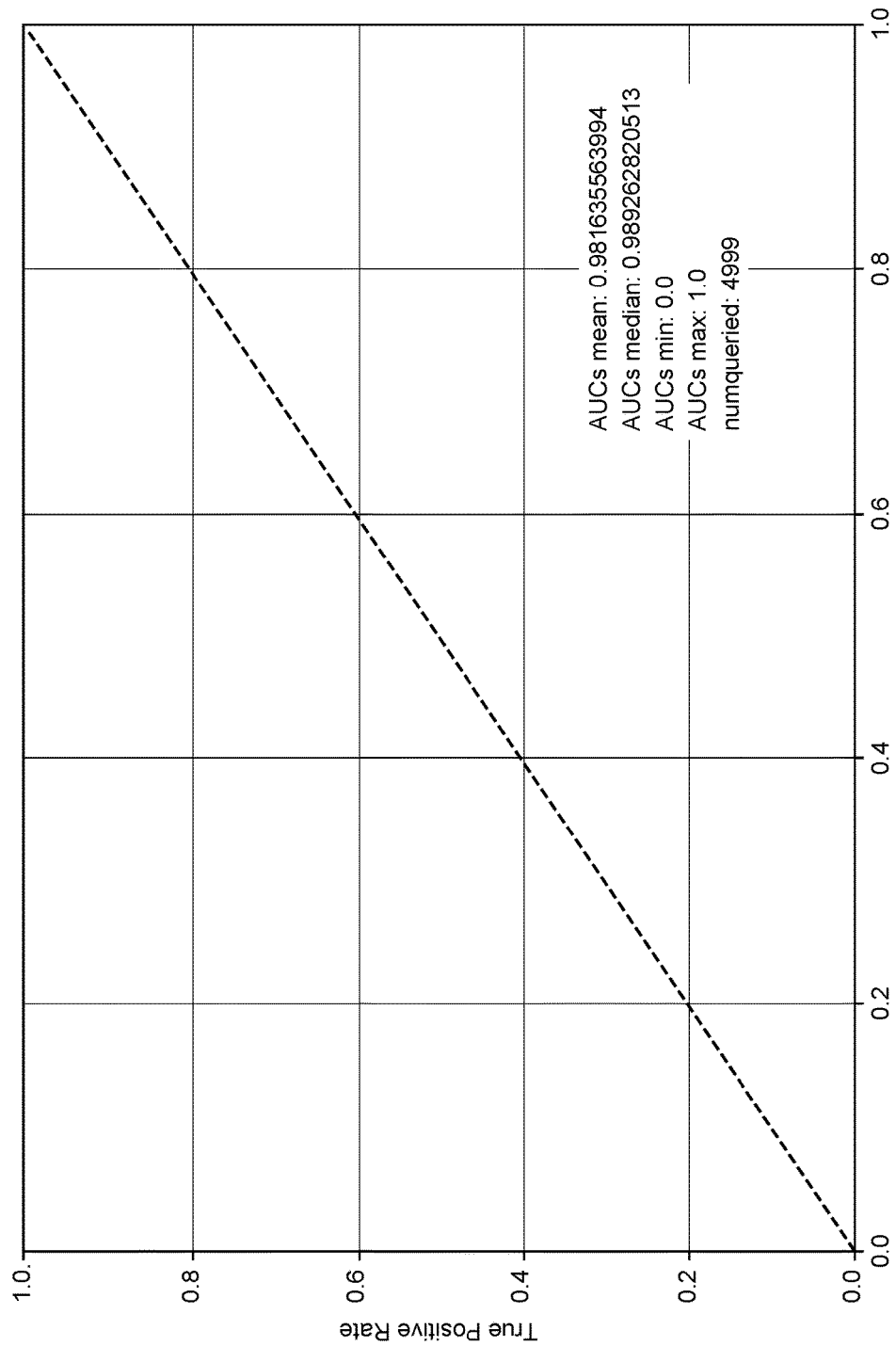

AUGMENTED REALITY AND BLOCKCHAIN TECHNOLOGY FOR DECISION AUGMENTATION SYSTEMS AND METHODS USING CONTEXTUAL FILTERING AND PERSONALIZED PROGRAM GENERATION

CROSS REFERENCE TO RELATED APPLICATIONS

The present patent application claims the benefit of U.S. Provisional Patent Application No. 62/440,924, filed Dec. 30, 2016, and titled "Personalized Program Generation System with Plan and Ruleset Stacking", U.S. Provisional Patent Application No. 62/440,689, filed Dec. 30, 2016, and titled "Dynamic and Feedback-Based Ecosystem", U.S. Provisional Patent Application No. 62/440,982, filed Dec. 30, 2016, and titled "Personalized Program Generation System with Adaptive Program Engine", U.S. Provisional Patent Application No. 62/440,801, filed Dec. 30, 2016, and titled "Contextual Filtering and Adherence Scoring Systems and Methods", U.S. Provisional Patent Application No. 62/441,014, filed Dec. 30, 2016, and titled "Deep Learning and Ingredient Identification Systems and Methods", and U.S. Provisional Patent Application No. 62/441,043, filed Dec. 30, 2016, and titled "Multivariate Causation Systems and Methods". The present patent application is related to Non-Provisional U.S. patent application Ser. No. 15/859,126, filed Dec. 29, 2017, and entitled "Deep Learning Ingredient and Nutrient Identification Systems and Methods". The present patent application is also related to Non-Provisional U.S. patent application Ser. No. 15/858,713, filed Dec. 29, 2017, and entitled "Augmented Reality Systems Based on a Dynamic Feedback-Based Ecosystem and Multivariate Causation System". All of the aforementioned disclosures are hereby incorporated by reference herein in their entireties including all references and appendices cited therein.

FIELD OF THE PRESENT TECHNOLOGY

The present technology relates generally to a dynamic and feedback-based ecosystem that provides tailored decision augmentation solutions for users such as augmented reality experiences and blockchain-based decision augmentation tokens. Underlying these decision augmentation and augmented reality systems are a plurality of individual feedback loops that provide users with adaptive health, wellness, productivity, activity and/or longevity programs that are being constantly adapted based on coded rulesets generated from empirical studies, personal biomarkers, genome, microbiome, blood test analysis, preferences, restrictions, beliefs and goals, as well as, sensor feedback, user feedback, external sources and input from multivariate causation analysis.

SUMMARY

According to some embodiments, the present disclosure is directed to a system of one or more computers that can be configured to perform particular operations or actions by virtue of having software, firmware, hardware, or a combination thereof installed on the system that in operation causes or cause the system to perform the actions. One or more computer programs can be configured to perform particular operations or actions by virtue of including instructions that, when executed by data processing apparatus, cause the apparatus to perform the actions.

One general aspect includes a method of receiving data, an image or a video stream of restaurant menus, ingredients, beverages, food products, groceries, supplements, medications or food labels from a mobile device camera; evaluating the data, image or video stream of the restaurant menus, ingredient lists, beverages, food products, groceries, supplements, medications or food labels by: determining the ingredients and nutritional content and attributes of the items that are indicative of nutritional values; and comparing the attributes to a personalized plan established for a user; and generating a personalized adherence score for each food item that can be delivered through an augmented reality overlay Other embodiments of this aspect include corresponding computer systems, apparatus, and computer programs recorded on one or more computer storage devices, each configured to perform the actions of the methods.

Implementations may include one or more of the following features. The method can include generating and displaying on the augmented reality overlay a dynamic adherence score for any of the restaurant menus, ingredients, beverages, food products, groceries, supplements, medications or food labels. The method can include where the dynamic adherence score is indicative of how well the item adheres to the personalized plan established by considering for the item any of required time lapse, periodicity, quantity, sequence, food and activity logs, sensors, external data sources, user context, and combinations thereof. The method can include receiving biometric or user-generated feedback; and updating the personalized plan established for the user based on the feedback. The method can include where the biometric or user-generated feedback includes any relations and specific sequences of foods, activities, symptoms, and outcomes. The method can include matching the image of the restaurant menus, ingredients, beverages, food products, groceries, supplements, medications or food labels to a source image in a database.

The method can include receiving a request for a recommended food, nutrition or health product stored in the database, the recommended product including at least one item that adheres to the personalized plan established for the user; displaying the recommended options using the augmented reality overlay or by giving the user relevant listed options; and calculating and displaying an adherence score that is indicative of how well the least one item that adheres to the personalized lifestyle and eating plan established for the user.

The method can include converting the source images or video streams into an augmented reality information overlay through a process pipeline (see FIGS. 10A-D) that does image correction, marker creation, and links each element to its nutritional component inference.

The method can include where the mLOM is used to generate a plurality of models, with each of the plurality of models predicting within a specific domain, further where each ontology is included of a plurality of labels associated with the attributes of the items that are indicative of nutritional values.

The method can include where the personalized plan is generated by: obtaining input from a multivariate causation system that includes lifestyle programs, dietary plans, nutrition plans, and empirical evidence-based programs; and selecting a dietary program for the user that is based on the input from the multivariate causation system and information of the user including genetics, biomarkers, profile, activities, background, clinical data, and combinations thereof. The method can include converting the lifestyle programs, dietary plans, nutrition plans, and empirical evidence-based programs into rule sets. The method can include creating a ruleset stack from a plurality of distinct dietary restrictions included in the lifestyle programs, dietary plans, nutrition plans, and empirical evidence-based programs, where the ruleset stack is further configured based on any of goals, biometrics, biomarkers, genetics, demographics, lifestyle and combinations thereof. The method can include prioritizing rulesets in the ruleset stack according to medical needs. The method can include where at least a portion of the lifestyle programs, dietary plans, nutrition plans, and empirical evidence-based programs selected for use are obtained from the database based on a comparison of the user to a plurality of other users with respect to any of goals, biometrics, biomarkers, genetics, demographics, lifestyle and combinations thereof. The method can include updating the personalized plan using empirical feedback gathered from the user or from biometric measuring devices utilized by the user. The method can include where the empirical feedback is processed using a low entropy causation function. The method according further including adapting the personalized plan according to relevant contextual information such as location, previous food, previous activity, current mood and stress level, sensor data, other external relevant data, and combinations thereof.

The method can include where personalized plan is created from any combination of personal goals, diet, program selection, preferences, restrictions, lab test results, biomarkers, sensor data, health information, demographics, daily activity, genome, microbiome, environment and personal information based on one or more selected rulesets.

The method can include generating a merged program or dietary plan for the user or a group of users based on multiple applied rulesets for the user or the user and additional users that also have individual ruleset based programs. The method can include where the personalized plan is updated using updated rulesets, empirical feedback, and active and passive feedback obtained from biometric feedback devices utilized by the user. Implementations of the described techniques may include hardware, a method or process, or computer software on a computer-accessible medium.

BRIEF DESCRIPTION OF THE DRAWINGS

FIG. 12 illustrates a table showing Receiver Operating Characteristics (ROC) curves for ingredient prediction according to embodiments of the present technology.

DESCRIPTION OF EXEMPLARY EMBODIMENTS

Figure 1:
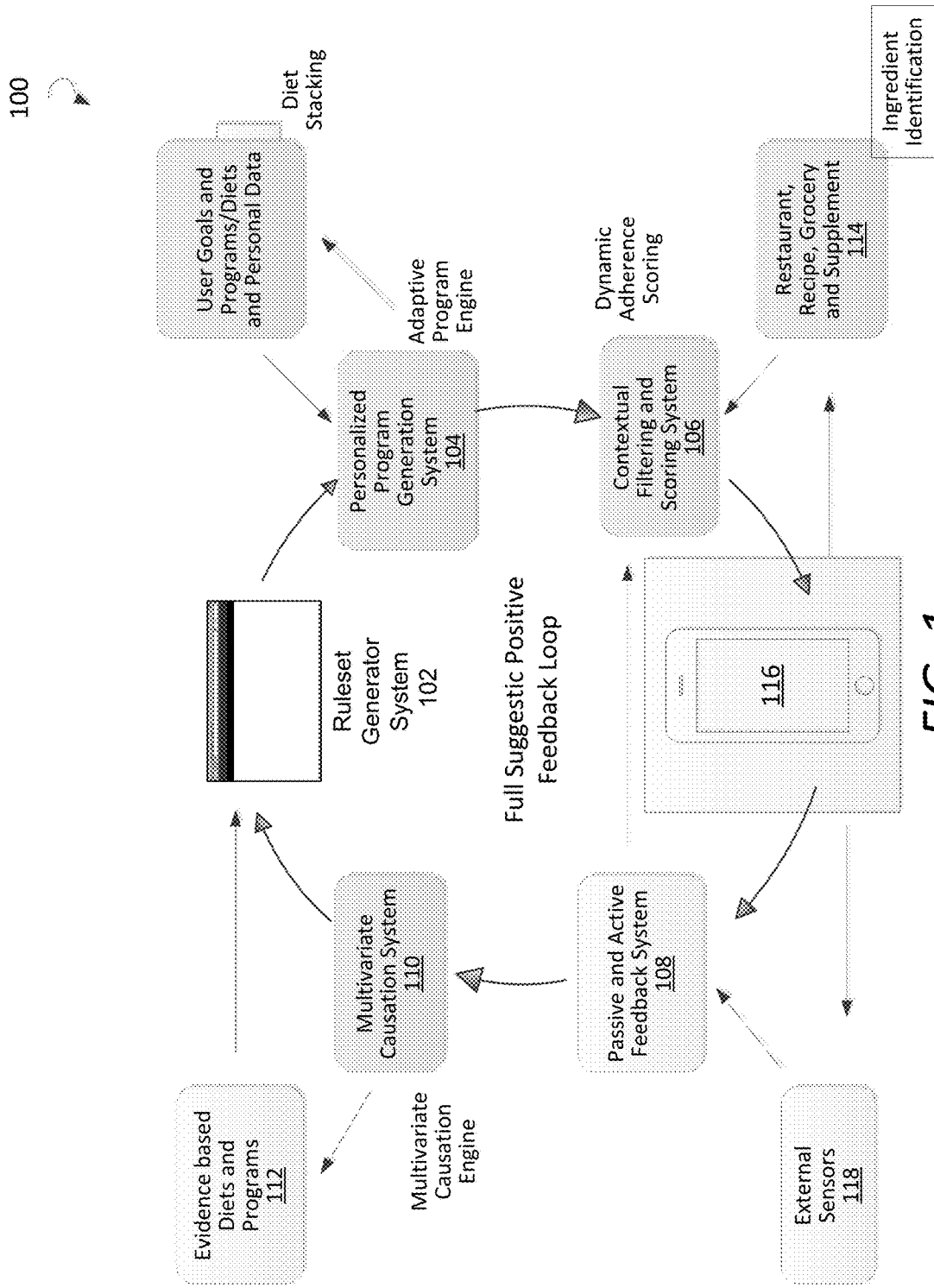
FIG. 1 is a schematic and flow diagram of an example system for practicing aspects of the present disclosure.

In general, the present disclosure provides for unique augmented reality (AR) experiences that assist users in creating and adhering to a plan. In some embodiments, this includes a dietary or lifestyle plan. In some embodiments, the augmented reality experiences provided herein allow a user to view restaurant menus, ingredients, beverages, food products, groceries, supplements, medications or food labels with a unique AR overlay that modifies and enhances how the viewer sees each item. This modification is based on the plan that has been selected and implemented for the user. In one non-limiting example, a user can utilize a mobile device with an AR application to view a restaurant menu with their mobile device camera. The AR application processes the individual items on the menu using machine learning or AI in order to determine the nutritional content of one or more items on the menu. Using the specifically adapted plan created for the user, the AR application can add an adherence score and highlight or block out menu items that do or do not adhere to the adapted plan for the user.

With respect to the overlay of AR on restaurant menus, ingredients, beverages, food products, groceries, supplements, medications or food labels, the overlay process is challenging since most menus are clear colored paper with little variability (except for the words themselves) and AR technology was not designed to lock onto text features, so standard AR technology is not feasible. Changes to the core functionality of an AR engine of the present disclosure had to be made to anchor the AR to the menu efficiently.

Enabling AR for each individual restaurant menu is improved when source images of menus are obtained. In some embodiments, this process can be facilitated by allowing end users to upload pictures of the menus or food items directly through the AR application.

Also, an automated process pipeline was created to convert these images into AR enabled restaurant menus and nutrition related items that match a database. FIGS. 10A-D collectively illustrate an example flow diagram of an augmented reality data creation pipeline (referred to as a "process pipeline").

In some embodiments, the AR menu experience is fully automated allowing users a near real-time experience of under five minutes, down to real-time or near-real-time, from the moment a picture is taken or the video stream is turned on, to having the AR experience delivered back to the mobile device.

Supporting the AR menu experiences is a dynamic planning application. This system that allows for personalization of each person's diet based on any nutrition plan they select. This plan is then optimized through tests (e.g., genome, microbiome, sensitivities, and so forth). The plan can be adapted through feedback loops that collect empirical evidence. An example dietary plan is encoded as dozens of individual rules that can be prioritized dynamically depending on factors such as a person's genes, microbiome or blood tests, as well as by data streams such as their last few meals, the number of steps they have taken or their blood glucose levels—just as an example.

Therefore, each person ends up with a personalized group of rules that are combined and prioritized dynamically. Every dietary plan is unique and alive.

Also, there is a long felt need in the industry to determine a method or system that will continuously learn and optimize every person's dietary plan by determining by means of scientific methodologies what is good for them (e.g., matches what actually works for their specific biological needs). Thus, every time a person eats, it can be thought as a small experiment in a sequence towards your goal. That is, each food consumed is a known quantity, and the biometric effects experienced by the user will dictate what that specific food or group of food does to the person in terms of, for example, biochemical responses or psychological responses.

The systems disclosed herein implement a continuous feedback loop that learns from each person's lifestyle and outcomes using a multivariate causation engine (MCE) that extracts this knowledge by learning the relations and specific sequences of food, activity, symptoms, and outcomes. The MCE learns from user activity and feedback to create new more precise rulesets. These enhanced dynamic rulesets combine with each plan to increase the efficacy of the desired goals and outcomes.

To be sure, generating a personalized ruleset or plan for a user is only responsive to a part of the need addressed above. The planning application of the present disclosure also allows for adherence determinations for a user. Every time an individual asks for suggestions for nearby restaurants that match their specifically tailored plan, the system will score hundreds of thousands of menu items before sending a response. In turn the system will consider the person's personalized ruleset which contains tens of thousands of individual attributes. The system then generates a score and queries a restaurant dataset by specifying quantities for hundreds of thousands of branded food products, thousands of ingredients, hundreds or thousands ingredient classification groups, hundreds of nutrients, and hundreds of other features like quantities, flavors, cuisine types, portion sizes, optional ingredients, and so forth. This is a task that is impossible for a human to accomplish in a time frame that is acceptable in the above scenario. That is, it is unacceptable for users to be expected to wait for days or weeks in order to receive suggestions that are appropriately tailored to their specifically adapted plan. It is entirely impossible for a human to consider the combinations and permutations of the categories listed above and make a decision that is meaningful to the user. This is especially true since restaurant menus change frequently, and the system must adapt based on this continually changing input variable. In some embodiments, the system can query over 30 million menu items with tens of thousands of attributes to give each user their personalized suggestions in real-time.

In some embodiments, adherence scoring is performed on a menu item basis. A salad with chicken may score an eight in a Mediterranean diet, but if a person were to eat a salad first and then a roasted chicken how much would both score together?

Some embodiments of the present disclosure address this issue by implementing a dynamic adherence scoring functionality that allows the user to have a score for their whole meal, their whole day, and their whole week. This type of dynamic adherence score will consider not only how adherent each recipe or menu item is to a user's personalized diet, but also, how adherent it is for the entire meal, day or week.

This also makes the diet suggestions richer by dynamically compensating for missing or excessive ingredients or nutrients.

Also, the systems and methods of the present disclosure can allow users to intelligently search restaurant menus. In these instances, the system will learn which ingredients and nutrients every menu item has, out of thousands of possible options. In most instances, restaurants do not publish the ingredients they use. And only around 800 chain restaurants in the US are required to make available a reduced set of 11 nutrients out of the hundreds of nutrients that the systems disclosed herein are capable of utilizing.

To be able to query over half a million restaurant menus, the systems disclosed herein implement an AI technology that learns to accurately predict every food ingredient, nutrient, flavor, portion, course, cuisine and quantity in any given menu item, food product or food label. The predictions generated by the systems and methods herein achieve over 98.5% of median area under the curve or AUC (an indicator of accuracy) in an ROC curve, and when compared with humans the system is almost twice as good in knowing which ingredients a menu item contains.

Figure 11:
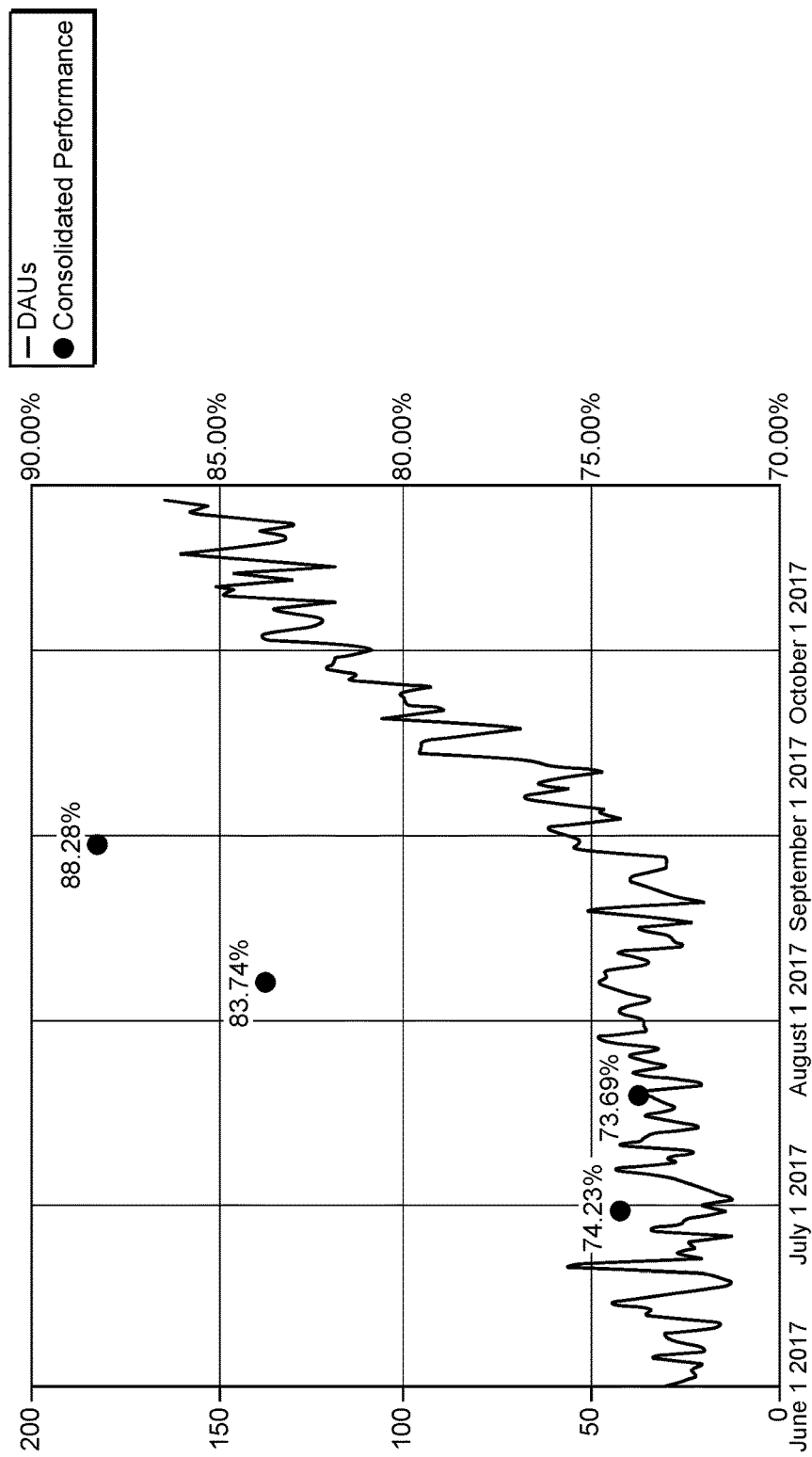
FIG. 11 illustrates a graph showing accuracy and performance of systems of the present technology as a daily active user number increased significantly over time.

This technology proved to be critical for users as illustrated in the graph shown in FIG. 11. The graph shown in FIG. 11 illustrates system accuracy and performance. As the system achieved better suggestions than what users would have found on their own, a daily active user number increased significantly.

In some embodiments, the systems and methods disclosed herein utilize a multi-model, multi-ontology, multi-label deep neural network (mLOM). mLOM is a specifically adapted AI that learns to predict restaurant menu nutrient composition from multiple points of view (e.g., models). Each of the models separately predicts within different domains (e.g., ontologies). And finally, each ontology is comprised of thousands of components and characteristics (e.g., labels). The result is that the better mLOM gets at predicting individual ingredients, the better it also gets at predicting related nutrients.

In some embodiments, the systems and methods herein are tuned to recognize portion sizes by restaurant depending on the price, type of restaurant, menu name, and so forth. This knowledge allows the systems to add specific nutrient quantities that are required in some diets and nutrition plans. Additional ontologies and labels are learned by the system over time to create better and more accurate experiences for the users.

Because of the multiple model nature of mLOM, the systems herein can add new "points of view" to analyze food. For example, the systems disclosed herein have the ability to recognize food plate images through a new model, that when combined with the knowledge the mLOM already has of food ontologies and food components, the system can predict ingredients and nutrients within images of food plates.

In sum, the present disclosure provides for systems and methods that possess several stacked layers of sophistication. At a threshold level the systems can predict very accurately nutritional composition of menu items. This in turn, allows the systems to create a searchable food universe. There are over 50 million menu items in the US alone that the system has make searchable. With these capabilities, the systems disclosed herein can be used to search and filter for highly specific personalized nutrition plans, as opposed to one-size-fits-all approaches like calorie counting.

Also, these layers collectively support and allow for the AR system to overlay this information through augmented reality experiences and extract menu information from menu images.

Addition implementation-level details and other objects of the present disclosure are provided in greater detail infra.

FIG. 1 illustrates an example ecosystem 100 of the present disclosure. The ecosystem generally comprises a ruleset generator system 102, a personalized program generation system 104, a contextual filtering and adherence scoring system 106, a passive and active feedback system 108, and a multivariate causation system 110. These various systems can be executed using, for example, a server or within a cloud-based computing environment. In some embodiments, each of the various systems of the ecosystem 100 can be consolidated into a single system.

In one embodiment, the ruleset generator system 102 obtains input from two separate sub-systems. In one embodiment, the ruleset generator system 102 obtains evidence based diets and programs from various sources 112. For example, this could include peer-reviewed or other similar publications or data regarding diets and exercise such as ketogenic, paleo, vegan, low carbohydrate, low-fat, or even specific dietary plans such as whole 30, Daniel Diet, and so forth. These programs or diets can also be submitted directly by researchers, healthcare professionals, user groups or individual users. These data are received by the ruleset generator system 102 and converted into rulesets that can be applied to a personal program for a user. For example, the ruleset can include rules for those persons with specific biomarkers or characteristics, with specific ratios of macronutrients that would be found in a particular dietary plan, as well as restricted or promoted food items.

The ruleset generator system 102 can also obtain input from the multivariate causation system 110, as will be described in greater detail below. In general, the multivariate causation system 110 can generate both updated evidence based data for the various sources 112, as well as ruleset updates that are each based on output of the passive and active feedback system 108. In general the passive feedback from sensors and external sources and active feedback from user input in system 108 is measuring empirical feedback from biometric resources or other applications that are tracking exactly how the user is behaving or acting based on the information given and plan established by the ecosystem 100. For example, if the user is following a prescribed plan that is designed to reduce weight but the user is not achieving results based on scale feedback received by the passive and active feedback system 108, the multivariate causation system 110 can assess the lack of progress and determine a change to the ruleset(s) that might positively correlate with an improvement towards the goal. For example, if a user desires to lose weight and has not done so, the multivariate causation system 110 might suggest that the user reduce caloric intake or potentially remove a food item from their diet or substitute one item for another in their diet to improve their outcome.

To be sure, the multivariate causation system 110 can utilize artificial intelligence techniques such as deep learning or machine learning or big data that include information from other users having similar genetics, biomarkers, profile, activities, background, clinical data or other demographic or personal information. Thus, the user is not only analyzed in context of their own personal goals and personal information, but the multivariate causation system 110 can also derive or infer new rules based on what has worked or not worked for other similarly situated individuals. In other embodiments of the multivariate causation engine it also includes any type of data streams or log data to derive or infer new rules based on the sequences and patterns found. The sequence or log data can include, but is not limited to sensors, test results, biomarkers, activities, symptoms, supplements, medicine intake, food, beverages or locations. The multivariate causation engine can also determine the likelihood that each pattern or sequence of events will have a predicted outcome.

The personalized program generation system 104 can utilize ruleset stacking to create a converging solution for a set of dietary considerations or limitations for a user. For example, if a user has dietary considerations of being a vegetarian, as well as being on a reduced-salt diet. The user also does not like certain gluten products. The personalized program generation system 104 can overlap these diets for a single user. In other embodiments the personalized program generation system 104 can overlap the dietary restrictions of multiple users to create a single converging solution for multiple parties.

The personalized program generation system 104 can also implement an adaptive program algorithm and create a personalized program for a user. The personalized program generation system 104 receives one or more rulesets that are applicable to the user based on information known about the user. For example, the user prefers paleo diet. Thus, the personalized program generation system 104 will obtain rulesets for paleo adherents and will further personalize each of the rules based on the user's information. The rulesets obtained from the ruleset generator system 102 can be selectively adjusted based on other information such as a user's genetic information, their microbiome, their biomarkers, their clinical, medical or health data, activities, their age, weight, height, ethnic background, other demographic information, and so forth.

In some embodiments, the personalized program generation system 104 can implement a data gathering process whereby a user is questioned using a chatbot or other means to obtain information that is used to select any appropriate rule set and goal for the user. To be sure, this can be augmented with more detailed information about the user such as specific objective and subjective demographic information, genetic test information, microbiome testing, lab test results, and so forth. This information can also be obtained from medical records, including electronic medical records. An example method for collecting user information comprises the use of a chatbot that is programmed to interact with a user to request diet preferences and health conditions, as well as a target goal(s). Another example is to obtain the user's permission to connect to their health application or service that will further enhance the personalization of their program.

The contextual filtering and adherence scoring system 106 is configured to execute dynamic adherence scoring algorithms to determine the adherence level of any meal or activity against the personalized program, diet or plan. It obtains information from external and internal sources such as restaurant and recipe sub-systems or databases 114. In some embodiments, the contextual filtering and adherence scoring system 106 obtains recipe, supplement, grocery, and restaurant menu information using deep learning and artificial intelligence information gathering techniques. The contextual filtering and adherence scoring system 106 can also obtain feedback on these types of information from user interaction with the ecosystem 100. This user feedback assists in resolving errors or inconsistencies with data.

According to some embodiments, the contextual filtering and adherence scoring system 106 can use specific techniques to examine menus, recipes, and ingredient lists from a wide variety of sources and correlate and/or harmonize what is known about individual meals, activities or places. In this way, the contextual filtering and adherence scoring system 106 can select appropriate meals or activities for the user based on their goals and personalized program.

The contextual filtering and adherence scoring system 106 provides personalized programs to the user through their computing device 116. The contextual filtering and adherence scoring system 106 provides the user with a personalized program that is tailored based on selection of lifestyle programs, dietary plans, nutrition plans, and empirical evidence-based programs that are converted to rulesets and applied to a user's goals, preferences, and demographics. Contextual filtering is applied in some embodiments to selectively tailor the recipe or menu suggestions provided to the user in accordance with their personalized plan generated by the personalized program generation system 104.

The computing device 116 executes a client side application that provides personalized plans and receives both passive and active feedback, in some embodiments.

In some embodiments, the passive and active feedback system 108 receives data from the user through the computing device 116. For example, the user can create a food log or record their exercise. The user can also take pictures of food, menus, ingredient lists, and so forth. This information can be fed back into the restaurant and recipe subsystems or databases 114. This gathered information can also be redirected back to the passive and active feedback system 108 for further analysis by the multivariate causation system 110.

In some embodiments, the passive and active feedback system 108 collects information from external sensors 118 from sensors such as wearables (e.g., smart glasses, watches, etc.), sleep sensors, blood pressure monitors, glucose monitors and insulin pumps, blood pressure sensors, respiration monitors, pulse oximeters, heart rate meters, and so forth—just to name a few.

The multivariate causation system 110 is configured to receive empirical feedback about the user and their behavior from the computing device 116 and the external sensors 118. The multivariate causation system 110 uses the specific information known about the user and those users who are similar in one way or another (goals, biometrics, biomarkers, genetics, demographics, lifestyle, and so forth), as well as feedback from the external sensors 118 to selectively modify how a user's diet is prioritized and potentially if rule sets are adjusted for the user. For example, as different users progress towards a goal, their passive and active feedback is analyzed by the multivariate causation system 110 that determines what has worked. It then modifies and reprioritizes the program rule sets so that the patterns and activity sequences that work best are suggested, and those patterns or sequences that do not work are reduced or avoided. The multivariate causation system 110 can adjust priority and/or rules for the diets and programs to more closely align with the goals of the successful users. The multivariate causation system 110 receives streams of data from user passive and active feedback, as well as the programs, goals and personal data and adjusts the rulesets on the fly or periodically.

Figure 2:
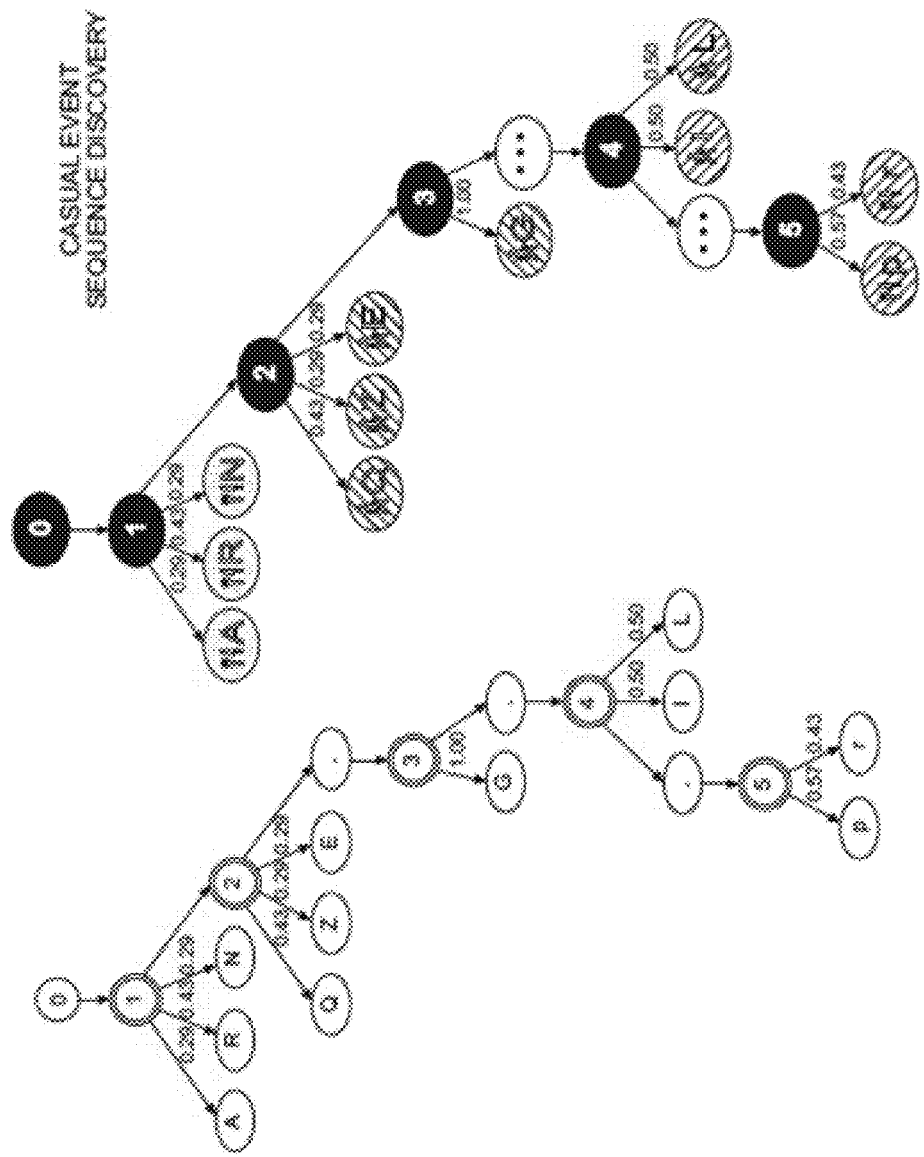
FIG. 2 illustrates an example causation sequence performed by the multivariate causation system.

The multivariate causation system 110 can also act as a data producing system that reports back information for use in the evidence based diets and programs from various sources 112. The multivariate causation system 110 can deeply analyze user feedback and determine specific variations on behaviors and determine how they affect the desired outcomes. For example, the multivariate causation system 110 may determine that the user moves closer to achieving a goal when they restrict carbohydrate consumption in the morning and evening, or if they eat vegetables as snacks as opposed to combining them with protein sources. FIG. 2 illustrates an example causation sequence performed by the multivariate causation system 110. The causal event sequence discovery is a process performed from events gathered from user behaviors and the external sensors 118 and the computing device 116.

With respect to causation, the systems and methods herein can implement one or more multivariate causal discovery techniques such as low entropy approaches for causal inference. Prior to describing these methods, a discussion will be provided that is related to human activity language or (HAL).

Human behavior can be simply described as a secession of activities or actions over time. These performed actions shape the observed state of a single person, as its health and perceived well-being. Understanding the relationship between human behavior and observable final outcomes is crucial to discover how users should behave in order to achieve certain goals. Actual behavioral rules still remain mainly based on deductive thinking, this is, we are encourage to behave the way we believe is the best way, even when a lack of evidence is present.

Recently, the developments of smart devices that log behavioral data, as user interaction with smart phone applications or wearable sensors open the opportunity to easily identify human activities at any moment.

Even though the sophistication of human activity recognition is evolving, little effort is being made to represent and analyze behavioral data. Once the activities are identified, typical processing approaches include time series analysis on single variables.

A framework to study human behavior should not be only friendly to store and analyze activity logs; it also should be directly usable by most recent developments in machine learning, which permits a wide range of predictive tasks and pattern discovery.

Additionally, theoretical advances in causality discovery from observational data allow a new kind of insights to determine direct effects of human activities, and any proposed human behavior framework should naturally fit the requirements of this kind of analysis.

Proposed herein is a standard language to describe human behavior, and direct methods to analyze this language from many current knowledge discovery approaches are also presented.

A key concept to appreciate is that any succession of activities can be seen as a succession of symbols or characters. This description deals with a problem of finding such adequate set of symbols, and the role of a grammar as a way to summarize the rules governing any observed sequence of activities.

In some embodiments, actions can be described as coarse or fine grained actions. The level of detail describing an action should be determined at any moment depending of the intended kind of analysis. This property only can be achieved if actions are considered as intrinsically hierarchical. From this hierarchical perspective, each level of description of an action corresponds to a node in a tree like structure. Any further level of description is represented as a child node, and a more coarse grained description as a parent nod In light of the above, a set of algorithms can be defined if A is a directed acyclic graph with the vertex set V(A) as the set of all possible action descriptions, and E(A) a set of directed edges:

$$(a,b) \text{ for } a,b \in V(\mathcal{A})$$

It is assumed that b is a detailed description of a. Let No define an initial node, and edges $(\mathcal{N}_0, x)$ to $E(\mathcal{A})$ for each activity description x with no parents (i.e., x is the most general description of an activity). Now, if we define $l: V(\mathcal{A}) \times V(\mathcal{A}) \to \mathbb{N}$ as the number of edges required to reach a node from another and we can define the level of description to any activity a as $l(\mathcal{N}_0, a)$. Given this setup, $R_c = \{a \in V(\mathcal{A}) | l \mathcal{N}_0, a) \leq c\}$, the variable c is the set of activities with description level c. The set of terminal activity definition symbols $S_c \subset V(\mathcal{A})$ with description level c may be defined as:

$$S_c = \{s \in R_c | \not\exists z \in R_c) a, z) \in E(\mathcal{A})\}.$$

It will be understood that any succession of activities can be straightforwardly represented as a succession of symbols in Sc at any desirable level of detail c. Implications of this fact are discussed in the following sections.

With respect to constructing an activity hierarchy, having a set of well-defined activities, the DAG hierarchical structure discussed above can be obtained in two ways. One option is to decide which activities represent a more general description of another. This directionality represents a partial order that naturally induces a DAG structure.

Another option is by clustering of activities given any activity similarity criterion. Note that even with the same set of activities, different activity similarity measures and clustering rules give rise to different DAG structures.

A representation of activities with a DAG structure possesses the additional advantage of having natural criteria to define a random variable and possible realizations.

This is, any parent activity can be seen as a random variable, and all child activities are the possible outcomes. Selection of activities to be treated as random variables can also be determined by the detail level parameter c described above.

Once defined the alphabet of human activities, any behavior can be represented as a concatenation of such activities or a string of activities. The first main property of this setup is the possibility to express the rules governing any desired behavior as a grammar. Also, given any activity string, there always exists at least one grammar able to generate such string.

The possibility to express any behavior as a grammar has the advantage to formally resume a set of deductive rules. Nevertheless, the ability to infer the grammar given a set of activity strings opens a new kind of human behavior analysis based on observational data and well established formal and natural language theories. Also, new developments on recurrent artificial neural networks allow the creation of generative models that approximate the rules of the unknown grammar behind observed activity strings.

Such generative models can be trained on any subset of activity strings, depending on the desirable final outcome to analyze.

With respect to behavioral similarity, there is proposed a manner in which to quantify similarity between two behavioral measures (i.e. how similar were the activities of two people during last day?).

Note that any subsequence shared by two activity strings denotes a same behavior, and explicit identification of such subsequence is equivalent to solve the maximal subsequence problem (MSP). Also, variations of this MSP can deal with more flexible measures of similarity by assigning a value of similarity between each pair of activities.

For example, a cost matrix C with $C_{i,j}$ being the similarity between activities i and j can be constructed by the sum of path lengths from activities i and j to the closest shared parent. MSP is a particular case with $C_{i,j}=k$ if i and j are the same activity and $C_{i,j}=0$ otherwise for some arbitrarily chosen constant k.

In some embodiments, the approaches disclosed herein can be utilized to measure behavioral similarity can be directly used as a kernel function.

Returning to aspects of causal inference, generally speaking, the concept of causality remains under debate from different disciplines, like philosophical, physical or social sciences.

Under a fixed concept of causality, causal discovery from data remains as an open problem.

It can be noted that the concept of entropy appears in some way in many of these approaches, either explicitly or by equivalent formulations.

This document describes how to apply minimizing entropy techniques in causal discovery. Two principal causation problem setups are discussed. One, in which static variables (i.e., not changing over time) are involved, and one in which dynamical variables changing over time in conjunction with other variables determine some output.

With respect to static variables, entropy measures as a causal discovery tool. If a high entropy variable X associated with some particular value of a target variable Y=y cannot be causal. Note that this statement does not imply that a low entropy variable must be a causal variable. In other words, it is necessary but not sufficient for X to have low entropy in order to be causal for Y=y.

For example, imagine that the proposed causal variable X describes what kind of drink you take before going to sleep, and the target variable Y describing the sleep quality. Fixing Y to be a "good quality rest", the worse scenario in terms of causality association is when X is realized to the values "vodka", "milk" or "coffee" exactly one third of the times Y equals "good quality rest", as it seems that the change in X actually does not have an effect on the target variable Y to be set as "good quality rest". In this scenario, the variable X has maximum entropy and we have no motivation to consider X as a cause of having a good quality rest.

It will be understood that the function P(y|do(X=x)) does not change for any x.

Also, lowest entropy in variables over each possible outcome implies the simplest predictive rules. In terms of machine learning algorithms, these kinds of data require the lowest complexity in any predictive model. Thus, any change on these ideal setup criteria are reflected in loss of accuracy, which is consistent with the idea of Granger causality.

The idea of entropy is directly used as a feature selection approach for classification, where a subset of features is expected to contribute the most to an accurate prediction, as high entropy relates with disorderly configurations and more complex decision boundaries.

Consider now that relating a set of variable realizations in a temporal sequence with a target variable realization is desired. Here, a low entropy is expressed as similarity between realizations and similarity in the ordering of these realizations.

We are interested in consistently finding patterns like "watch tv, then take a shower, then play whatever game on your phone and then drink whiskey" whenever you have a good quality rest. It can be said that these sequence of activities have low entropy under the desired output Y="good quality rest", so, this sequence cannot be discarded as a causal activity sequence.

Using the HAL framework described above, assigning a symbol to any particular activity allows the representation of any sequence of activities as a sequence of symbols. In some embodiments the rules governing a temporal activity pattern, as the grammatical rules used in every-day language. In fact once this representation is adopted, all formal language theory can be applied.

Assuming only a set of activity sequences and some measurable effect of performing these sequences are provided, groups of sequences that causes effects can be determined. Next, the question that is answered is what are the most important activity patterns that cause the actual effect? Recalling the arguments about lowest entropy, the system will find some sub-sequence that is conserved among the set of sequences of interest.

Another important question is, what are the rules governing the realization of such activities? Some approaches to construct generative models that approximate the unknown rules, such as Long Short Term Memory recurrent neural networks, the Cortical Learning Algorithm in Hierarchical Temporal Memory theory and Hidden Markov Models—just to name a few.

Additionally, given a set of activity sequences, a pattern among these sequences should be based only on the subset of activities that are conserved between all sequences. For example, consider the following sequences 'abi', 'agb' and 'eabp'. The presence of the activity 'a' is followed in time for the activity 'b'. Thus, this pattern is called a pattern because it appears consistently among all considered sequences. This pattern can be visualized in the alignment of the activity sequences:

| 1 | 2 | 3 | 4 | 5 |
|---|---|---|---|---|
| — | a | — | b | i |
| — | a | g | b | — |
| e | a | — | b | p |

In this alignment, gaps (denoted as -) are inserted as necessary in each sequence in order to align the activities 'a' and 'b' in the columns 2 and 4. Note that this alignment results after the insertion of gaps among the sequences and there are infinite ways of inserting gaps in the sequences. The construction of the alignment depends on deciding in which particular positions are the gaps required to be inserted in the sequences in order to align the same activities.

If the set of possible alignments is denoted by A, a cost function: $C:A^* \to \mathbb{R}$ This function quantifies how well an alignment is formed. A good alignment (low cost) is the one that contains many columns with the same activity (or very similar activities) among the sequences in each column. A bad alignment (high cost) is an alignment that has columns composed of very different activities and gaps. In this way, C is just the sum of individual column costs. Also, a column cost depends on the direct pairwise cost between activities.

If $\Sigma$ is the alphabet of activities, the cost function is used:

$$c: \Sigma \times \Sigma \to \mathbb{R}$$

This function quantifies the direct similarity between any pair of activities. Application of this approach was first proposed in [Needleman and Wunsch 1970] to align biological sequences. The Needleman and Wunsch algorithm applies dynamic programming using the pairwise cost function c to compute a global alignment. As aligning gaps along with activities in each column supposes a high cost, large gap islands are highly penalized and the resulting alignment may be the one that minimizes gap alignments instead of maximizing activity alignments. Later on, Smith and Waterman [Smith and Waterman 1981] proposed a variation to the Needdleman and Wunsch algorithm that finds local alignments. Numerous improvements to these algorithms have been made since then with a very high bias to analyze only biological sequences. Alignment algorithms have also being independently developed in image analysis, giving rise to techniques like image stitching, that combines many overlapping images in a single one.

In some embodiments, hidden markov models (HMM) can be created from activity patterns. Given a sequence alignment, a HMM can be constructed in such a way that each alignment column defines a hidden state, with emission states as the set of activities in such column. Such HMM represents a model abstracting the consensus behavior of the original set of activity sequences. For example, consider the set of activity sequences:

{'uabiabo','labkabj','mabgabd'}.

Figure 4:
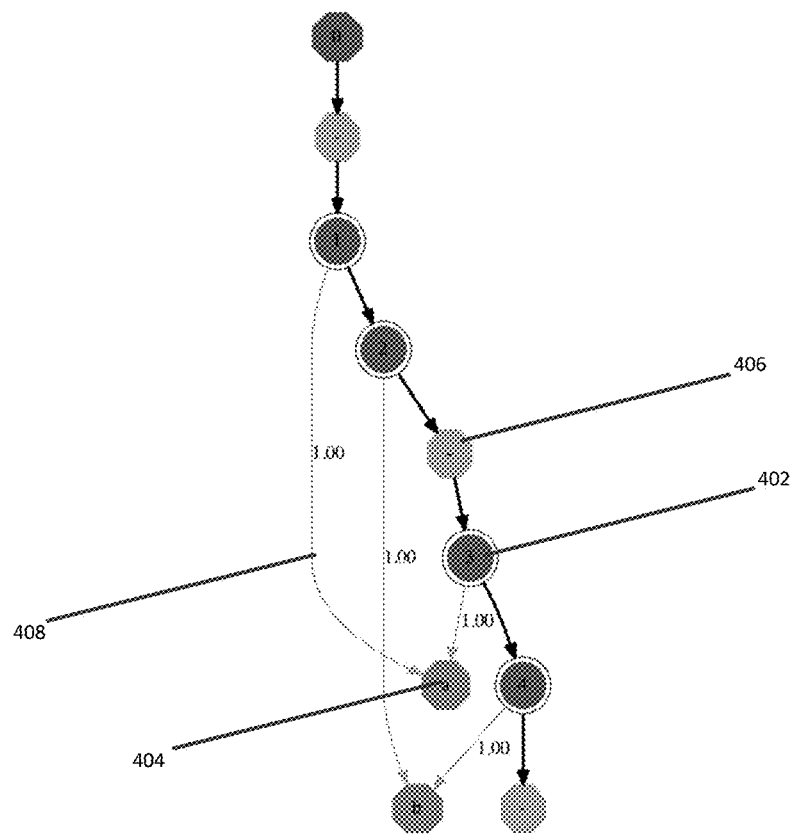
FIG. 4 illustrates an example hidden markov model sequence pattern.

In this case, the sequence pattern found in these sequences is: "a followed by b followed by something else, then a followed by b again". This pattern form of an HMM is depicted in FIG. 4, where states are represented by red circles such as circle 402, connected with activities in orange such as 404. Gray nodes such as node 406 represent states that allow any activities. Bold arrows such as arrow 408 between states represent the temporal flux of states.

Figure 5A:
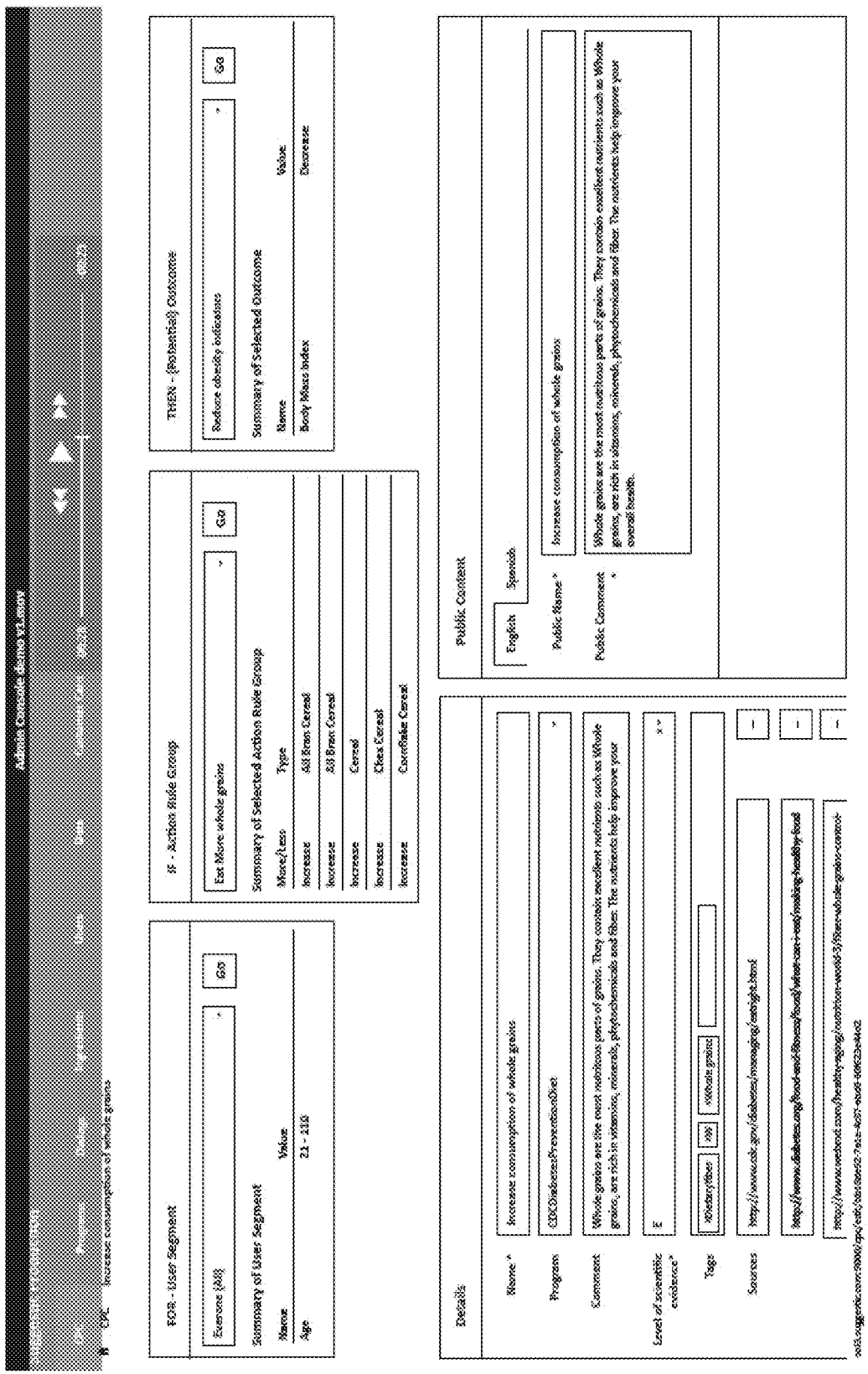
FIGS. 5A-C are each screenshots that collectively illustrate creation of rulesets based on empirical data.
Figure 5B:
Figure 5C:

FIGS. 5A-C collectively illustrates creation of rulesets based empirical data, as well as detailed GUIs that illustrate the applicability of a ruleset to a given individual (based on ethnicity, genetics, or other categories) and specific cause and effect scenarios such as "if a certain action is taken", a "beneficial result(s)" will occur based on the behavior for that particular type of individual.

At this point, it was shown how to extract a pattern from a set of activity sequences associated to a particular outcome. Nevertheless, with this information alone it is not possible to ensure that the pattern found actually causes the observed outcome.

In this instance deterministic causality is not considered. This is, if a is said to cause b, then b needs to be preceded by a. Under this definition, war does not causes death, nor smoking cause cancer. Probabilistic nature of causality introduced by Suppes requires that if a causes b, then $P(b|a)>P(b)$, nevertheless, this approach does not take into account any other possible causes to a. Explicit inclusion of these additional factors are rendered in Cartwrights criterion as: $P(b|a,k)>P(b|\neg a,k)$.

Here, three random variables are required. In order to use this probabilistic definition, some additional formalism is required to express HMMs obtained from activity sequences as possible realizations of random variables a and b. As random variable k represents any external influence, explicit definition is not required.

First, suppose a vector space $V^n$ over field R with each orthonormal basis vector representing a symbol in the activity alphabet. Now, consider the algebraic variety defined by:

$$P=\{(v_1, v_2, \ldots, v_n \in V^n | v_1 + v_2 + \ldots + v_n - 1 = 0\}$$

which has co-dimension one (1) respect to $V^n$. Now, each $p \in P$ represents a probability mass function over the activity alphabet symbol set. Now, any HMM can be seen as an indexed set of points in P.

Referring back again to FIG. 1, the components of the ecosystem 100 work together in a collective and synergistic manner to provide a user with empirical and evidence-based plans for improving their health. The ecosystem 100 leverages the human language and causality features described supra, and also incorporate the use of a mLOM architecture to process multi-variable, multi-ontology and multi-label data.

The ecosystem 100 uses various feedback loops (represented by the individual systems of the ecosystem 100) to create an environment that learns based on empirical feedback and fine tunes a plan for a user based on this information.

In further detail with regard to the contextual filtering and adherence scoring system 106, the present disclosure can be utilized to provide the user with robust suggestions and information from contextually relevant and actionable activities, recipes, groceries, restaurant menus, food, beverages, supplements, medicines and other similar items or actions. In some embodiments, the contextual filtering and adherence scoring system 106 receives a plan for a user from the personalized program generation system 104 and adapts the plan according to the relevant contextual information such as the location, previous food, previous activity, current mood and stress level, sensor data or other external relevant data. For example, it suggests meals or recipes for a user based on a comprehensive knowledge base of recipes and menu items from the restaurant and recipe sub-systems.

In some embodiments, the contextual filtering and adherence scoring system 106 is configured to provide what is referred to as dynamic adherence scoring. This process involves scoring any type of activity, food, beverage, supplement or medication in relation to how much it adheres to the user's optimal ruleset (personalized program). It takes into consideration for each individual action or item defined within the user's personalized program (food, activity or other) what the required time lapse, periodicity, amount and sequence should be. With these attributes it searches given the user context (location, time of the day, sensor data, recent logs, and so forth) to score all of the contextually relevant items or actions with an adherence score. The adherence score represents how close actions or items (individually or as a group or sequence) are to the personalized program ruleset.

Returning back to FIG. 1, the personalized program generation system 104 is a specific sub-system and feedback loop of the ecosystem 100. The personalized program generation system 104 receives rulesets from the ruleset generator system 102. A ruleset is created from an evidence based diet or program by converting a diet into actionable rules. Each rule is composed by several elements: Who? (e.g., a target user segment), When? (e.g., a target condition), What? (e.g., an action to execute) and finally, What should happen as a result? (e.g., an expected outcome). For example, a ketogenic diet would include a rule such as: for a target user segment (those with body weight within a specific range), for a target condition (at each meal or every X hours), action to execute (consume at least X number of grams of fat) with the expected outcome (maintain ketogenic state). The rules within the ruleset can be coded from empirical knowledge, from personal beliefs or can be generated or modified by the multivariate causation system 110 based on previous successful user outcomes.

The personalized program generation system 104 will use the specific target user segment and the personal data from the user to select and adapt the rules within each ruleset to each individual. For example, the personalized program generation system 104 can personalize a plan based on the user's goals, program selection, preferences, and restrictions, as well as based on their biomarkers, sensor data, health information, daily activity, genome, microbiome, environment, etc.

In another embodiment, the personalized program generation system 104 can select or adapt a ruleset for a user based on their empirical or known medical history and/or goal selected. For example, if the user desires to lose weight, the personalized program generation system 104 may select a low carbohydrate ruleset and adapt those rules based on the user's demographic, genomic, microbiome or health related information.

In another example, if the medical history for the user indicates that they have celiac disease, the personalized program generation system 104 can suggest and personalize, for example, a paleo diet that restricts gluten consumption and further alter the Paleo diet to avoid non-obvious gluten.

In some embodiments, the ruleset selected or adapted for the user is based on data collected from other similarly situated users. For example, the personalized program generation system 104 can select rulesets for the user based on similarities in the user's genetic information and other users who have similar genetics and have used the selected rulesets to accomplish the same goal. For example, if the user desires to change their blood pressure profile, the personalized program generation system 104 can look for rulesets used by other similar or bioidentical users that reduced their blood pressure with a specific diet and exercise regimen. As mentioned above, this can include not only dietary information but specific consumption information, such as how and when foods are consumed over time. For example, it may be determined that consuming breakfast within at least 30 minutes of waking up was beneficial for users.

In sum, the personalized program generation system 104 provides a positive, goal based suggestion/recommendation loop where the user is continually being monitored and adjustments are made to their program based on their personal data, their passive and active feedback, as well as their adjusted rulesets.

In some embodiments, the user goals, programs, diets, and personal data are obtained. In one embodiment, a single user may indicate that they want or need to follow several diets or programs simultaneously. This can include rulesets due to a health condition(s), to personal beliefs, to personal tastes, or based on different test results, sensors or data such as biomarkers, sensor data, health information, demographics, physical activity, environment, genome or microbiome. These facets may result in the selection of multiple dietary rulesets for a user.

The personalized program generation system 104 can also accommodate multiple rulesets for a user or multiple users. As mentioned above, this can include, for example, selecting a ruleset based on a plurality of health/dietary requirements that are based on medical knowledge of the user and/or personal preferences. In one example, the rulesets are based on genetic knowledge and/or microbiome information for the user, as well as personal food preferences of the user. In another example, a user may stack all his family member's diets to have one unique shopping list that considers everyone's needs and preferences.

With respect to diet stacking, the personalized program generation system 104 can not only overlay diets and find a single converging dietary solution for the user, but also create a prioritization for the user or update recommendations for the user based on their previous actions or goal accomplishment. This process is generally referred to as an adaptive program engine. The user's suggested diet can be automatically altered over time (e.g., days, weeks, months . . . ) based on places the user frequents, foods they consume and enjoy, foods and exercise regimens that provide desired results, and so forth. For example, the ecosystem 100 can monitor user response when a Gala apple is consumed with or without meals, or potentially during different times of the day.

In one example of stacking, the user is simultaneously following the Low Carb Mediterranean Diet the American Diabetes Association Guidelines because of his pre-diabetes, and has optimized his diet based on his genome by adopting a nutrigenetic diet. All three dietary rulesets will be stacked and merged into a final program.

In general, food, activities, restaurants and menu items that comply with the personalized plan for the user are preferentially selected for the user. Each menu item, product, recipe or activity is compared to the users personalized program and an adherence score is calculated. The adherence score takes into consideration the temporal and contextual requirements that the person may have. Continual tracking and reprioritization is used to adjust the user's plan during the day. For example, if the user is required by a ruleset to consume 40 grams of fish per day and the user has not consumed any fish by midday, the personalized program generation system 104 can re-prioritize fish consumption and prompt the user to consume fish at their next meal. This causes a re-stacking and re-prioritization of meal components, even if only for a single meal, day or week. This simultaneously happens for all the activities, ingredients, macronutrients and micronutrients required by the user's personalized program.

In some embodiments, the adherence score will have multiple inputs to generate the score. Inputs considered include the user personalized program ruleset, food log, activity log, sensor data, external data sources as well as contextual data such as the user's location, time of the day, day of the year, among others. All these data points and streams are translated into a standard list of optimal activities, ingredients, nutrients and products, which in turn are prioritized based on optimal time lapse, periodicity, quantity and sequence. The result is an adaptive adherence score that changes based on what a user is doing, eating or drinking, as well their mood, stress or current biomarker levels. For example, a user's adherence score for the same meal, two nights in a row could change dramatically based on how well he slept, how much exercise he did, what he had for breakfast or his current blood sugar levels.

In some embodiments, the adherence score can be calculated also for groups and sequences of items and activities. The adherence score is calculated based on external triggers, temporal windows, and periodicity for each activity and item. For example, some nutrients can be required at every meal, some others only once a week and some others may be triggered every time the user has drank alcohol the night before. This can allow for certain food or activities to be suggested given the user context and lifestyle. The optimal adherence score may require several items or specific sequences to be met in order to increase the overall score. For example, if a New York steak has a low adherence score for a user based on their personalized diet, the adherence score for the day could probably still be increased by adding a salad to the meal and having a 15 min walk afterwards.

Figure 3:
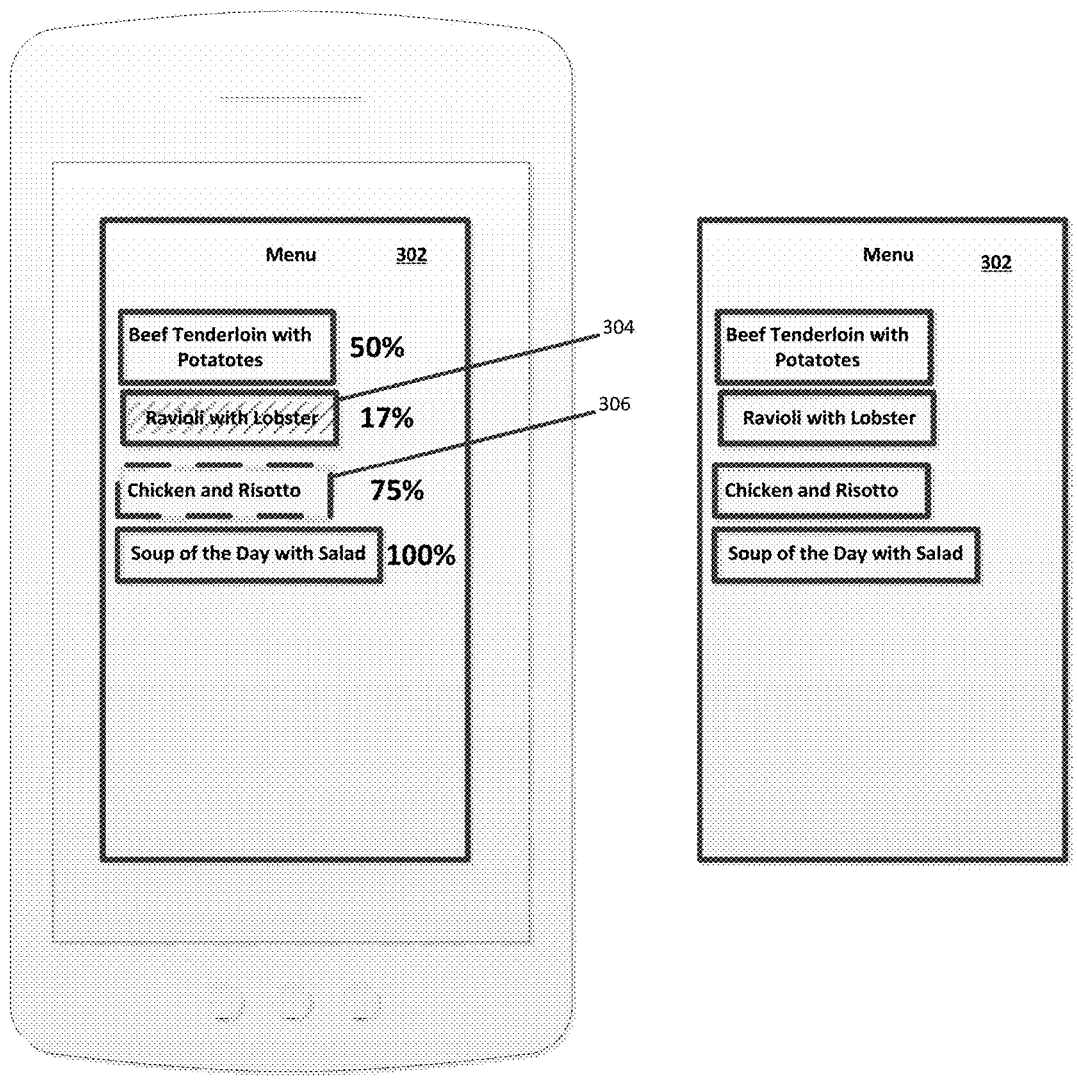
FIG. 3 illustrates an example AR overlay on a mobile device that is configured in accordance with the present disclosure.

As illustrated in FIG. 3, the contextual filtering and adherence scoring system 106 can provide information to the user through a chatbot, a graphical user interface, any messaging medium (SMS, email, written document, etc.) and in some embodiments a augmented reality interface.

FIG. 3 illustrates a mixed or augmented reality interface. This interface is created by obtaining a video or image of a menu 302 of a restaurant. The contextual filtering and adherence scoring system 106 obtains textual information from the image from for example, optical character recognition, or other text extraction methods. The contextual filtering and adherence scoring system may also derive the menu from its database, taking into account geo-location and temporal elements. The contextual filtering and adherence scoring system 106 will compare these menu items to the knowledge base and suggest menu items in accordance with the user's adaptive plan. For example, if the user is allergic to seafood, the contextual filtering and adherence scoring system 106 can identify menu items with seafood and those without and suggest non-seafood menu items.

In some embodiments, permitted menu items are highlighted in a first color, whereas impermissible menu items are highlighted with a second color or are blocked from view. Additionally contextual information may be overlaid to help the user through their decision process. Overlaid information may include, but is not limited to: adherence score, allergens, favorites, special items, quality, price, user feedback, etc. For example, the menu item of "Ravioli with Lobster" is highlighted differently from other menu items that are acceptable for the user and it may contain allergen information pointing out that it contains gluten. These menu restrictions can be based on the diet stacking methods described herein, where menu items that are acceptable based on the user's multi-faceted dietary requirements are suggested.

Figure 8A:
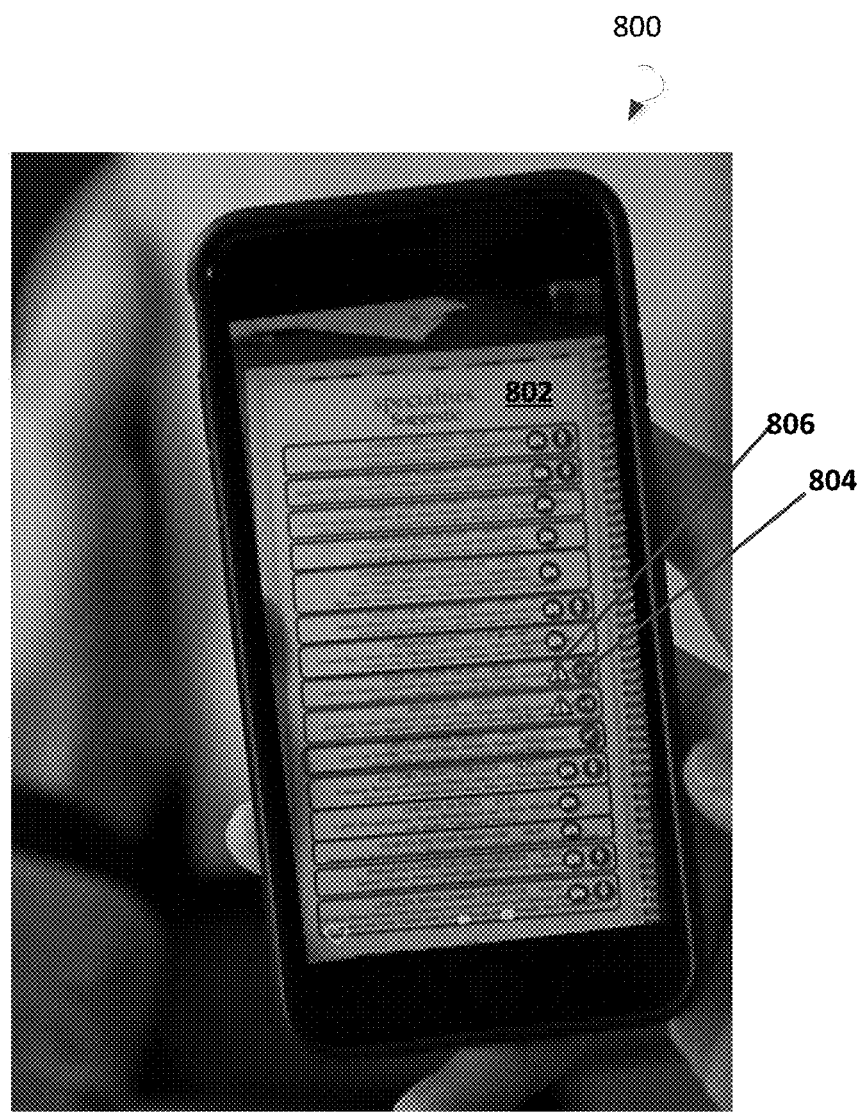
FIG. 8A illustrates an example AR overlay on a mobile device that is providing a view of a menu.
Figure 8B:
FIG. 8B illustrates an example AR overlay on a mobile device that is providing a view of an item on a store shelf.

In this example, the menu 302 has an AR overlay that highlights a menu item 304 with a very low adherence score of 17% and draws lines over the menu item 304. Conversely, the system calculates that item 306 has a relatively high adherence score. Other items are also scored to enable the user to select from the many options available. Additional AR GUI examples are illustrated in FIGS. 8A-B.

The personalized program generation system 104 can also prioritize rulesets when multiple rulesets are present. For example, it may be necessary to prioritize dietary suggestions that will result in blood pressure or blood sugar stabilization over personal food preferences or other similar preferences like vegetarian or vegan. This is referred to as a medical need.

As briefly mentioned above, the systems and methods herein are configured to utilize a multi-model, multi-ontology, multi-label deep neural network architecture. For context, in view of the rapid development of high-level libraries for deep learning, architectures are needed to boost prediction accuracies. It is also advantageous to combine known good performant architectures simultaneously with many knowledge sources for a base data set of the system.

Extreme multi-label learning refers to learning label sub sets for particular objects from a huge base label set. This task is different from multi class learning, when output is expected to be only one of many mutually exclusive labels. The mLOM architecture disclosed herein provides for multi-label learning setup that is extended to multi-ontology labeling, where labels may belong to different ontological domains. Multi-ontology label learning exposes two apparently opposite challenges in contrast with simple multi-label learning. First, knowledge from different ontological domains is transferred to others, and labeling under a particular domain is fine-tuned to concentrate in specific domain characteristics. It will be understood that an ensemble of different heterogeneous approaches usually out-performs single models. Thus, a unified way to synergistically combine such different approaches offers an overall superior predictive performance. Thus, the mLOM architecture of the present disclosure implements a deep neural network architectural model that handles simultaneously with multiple ontologies and multiple learning models, knowledge transfer for extreme multi-label learning.

In one example use case, it is desired for the system to infer food related labels from meal names only. These labels can be ingredients, for example. The system must be capable of multi-label learning, which comprises learning label subsets of particular objects from a base label set. This task is different from multi-class learning, where an output is expected to be only one of many mutually exclusive labels.

At the same time, relevant labels can belong to different ontological domains, like courses and cuisine type, additionally to ingredients.

Multi-ontology label learning exposes two apparently opposite challenges in contrast with simple multi-label learning. First, knowledge from different ontological domains should be transferred to others, and labeling under a particular domain should be fine-tuned to concentrate in specific domain characteristics. Additionally, some approaches may be better suitable for data or ontological complexity.

To be sure, an ensemble of different heterogeneous approaches usually outperforms any given single model. Thus, a unified way to synergistically combine such different approaches offers an overall superior predictive performance.

The systems disclosed herein implement a unique architecture that could handle these kinds of tasks. In some embodiments, a mLOM architecture utilized herein incorporates knowledge from m base models, each performing multi-label learning over ontological domains. A principal objective of the mLOM architecture is to simultaneously learn how to transfer multi-ontology knowledge inside each model and across different models. To be sure, in this disclosure, an ontology domain is also referred to generally as either ontology or a domain. Base models are defined as any neural network able to perform multi-domain multi-label learning, which means that output neurons should represent label scores for the entire label set.

To extrapolate knowledge from inferences made inside a domain to any other, the system implements a multi-ontology merging block. Multi-ontology merging block takes label scores from different domains from a base model as input and outputs same labels after some transformation layers to optimize again respect to expected output.

To combine knowledge from different models and fine tune single domain label estimates, all layers from different models for each domain are merged. Then m+1 additional layers are added to a fine tune layer stack. At each fine tune layer, a highway to each model is merged in such a way that raw model output can be rescued before additional transformations. This fine tune step is utilized to obtain a consensus from the different base models considered.

As an additional input for the fine tune, the mLOM will utilize output from a variational auto encoder (VAE). The VAE is trained with observed label sets for each ontology used by the mLOM. In this way, the system can ensure that any given label set is more consistent with observed ones. By way of example, if the input includes adding lettuce, tomato, onion and chocolate, the chocolate would be removed from this label set, as there are not examples of meals containing chocolate and lettuce as ingredients.

Figure 6:
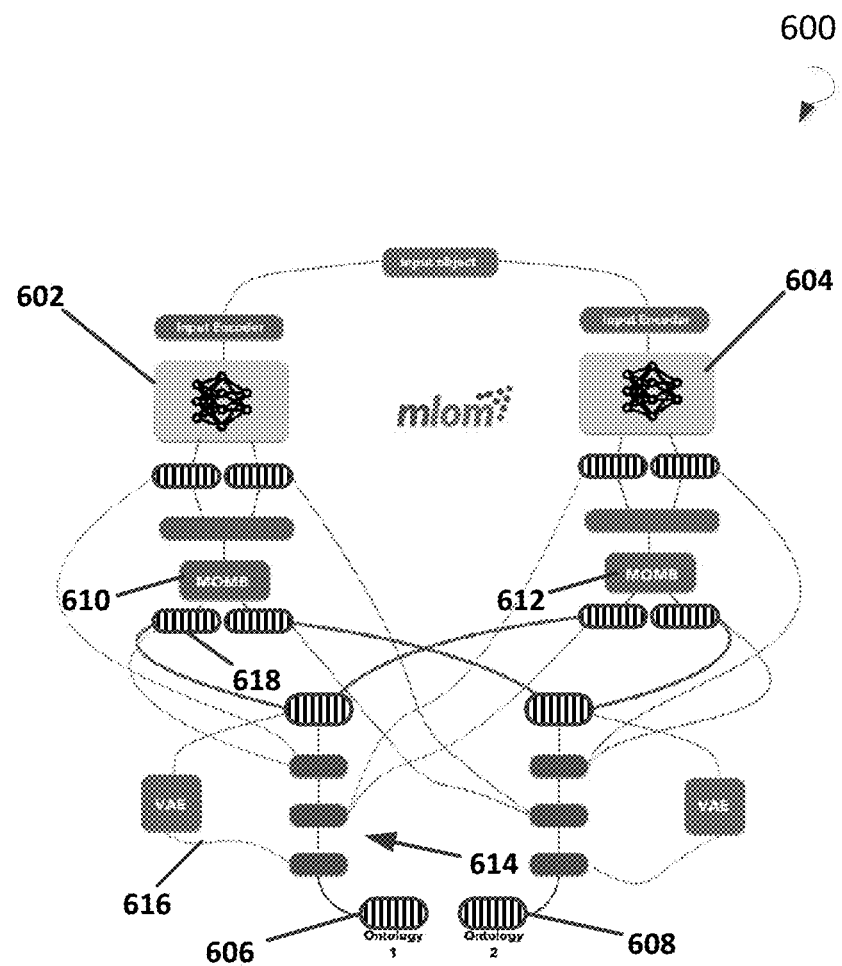
FIG. 6 is a schematic representation of an example mLOM architecture.

FIG. 6 illustrates a schematic representation of an example mLOM architecture 600. The architecture 600 for two base models 602 and 604 and two ontologies 606 and 608. An initial object is transformed with an appropriate input encoder for each base model. Raw output from each base model among different domains is taken as input for a Multi Ontology Merging Block (MOMB). Each base model will have an associated MOMB, such as MOMB 610 and MOMB 612. These MOMBs comprise additional layers that can refine independent domain predictions taking into account information from all domains being considered. A fine-tuning step is comprised of a stack of layers, such as layers 614 for each domain. Corresponding domain outputs from different base models are connected by highways (dotted lines, such as dotted line 616). Some layers have an associated loss function, such as layers illustrated in vertical cross hatching as with layer 618. As noted above, with this approach the system achieves 0.98 AUROC scores for ingredient prediction.

The table shown in FIG. 12 illustrates ROC curves for ingredient prediction. Each ROC curve represents the output for each meal in a validation set.

Figure 7:
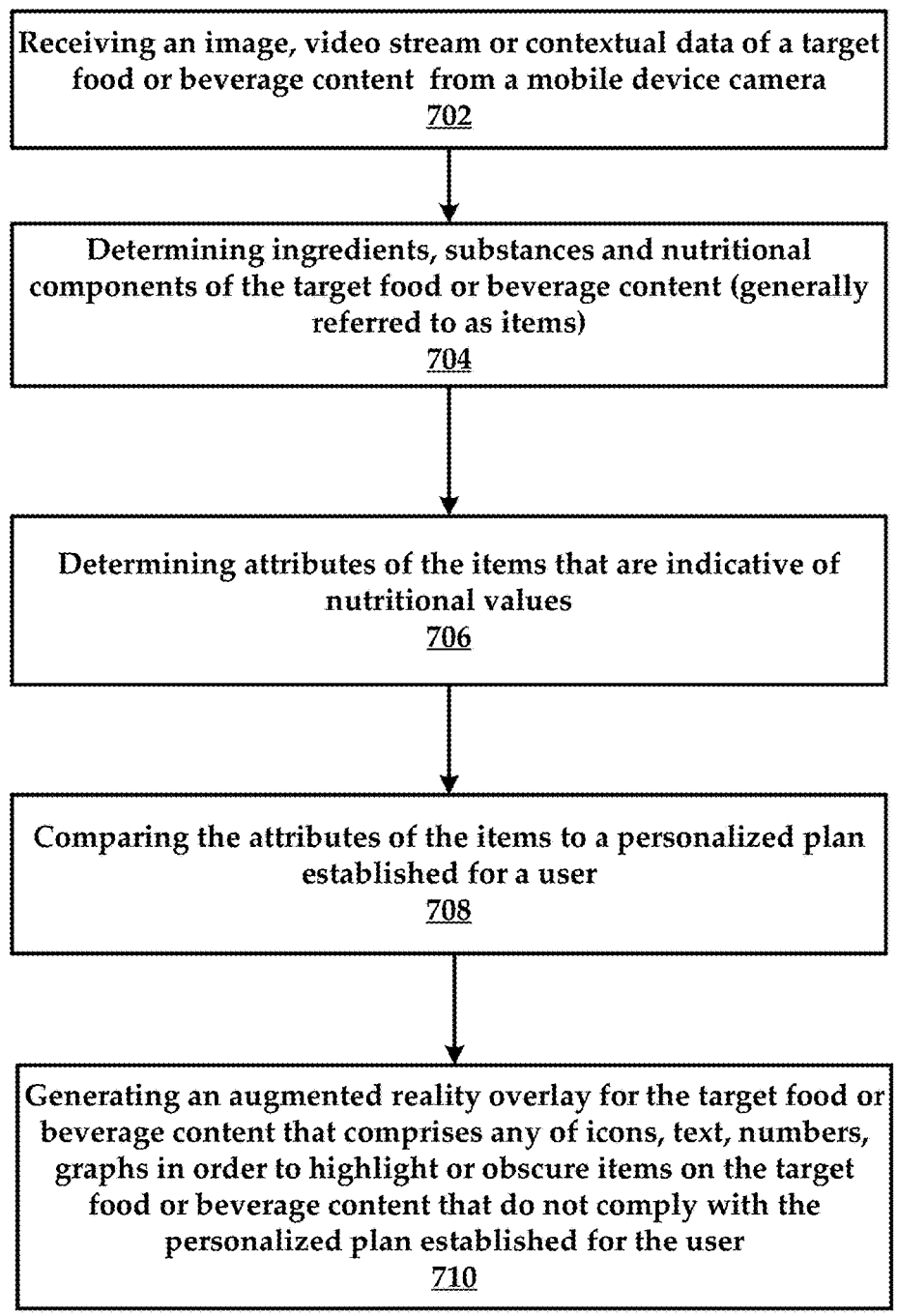
FIG. 7 is a flowchart of an example method of providing an AR overlay in conjunction with the personalization plans of the present disclosure.

FIG. 7 is a flowchart of an example method of the present disclosure for providing an AR experience to a user.

In various embodiments, the method can comprise a step 702 of receiving an image, video stream and/or contextual data of a target food or beverage content from a mobile device camera. For example, a user can hold their phone up to a menu (target food or beverage content) at a restaurant. Using the camera of the phone, the user can view the menu. This menu is received by an augmented reality application executing on the phone (or through a remote service or cloud that hosts the augmented reality application).

The contextual data used herein can include any of contextual filtering methods disclosed herein, and can include any context data obtained from a user or their device that executes the AR application. For example, using location data obtained from a user's Smartphone that is executing the AR application, the AR application can automatically determine data is relevant to that location. For example, the location is associated with a restaurant and an AR enabled menu has already been generated for that restaurant. In another example, a user can enter a grocery store with the SmartPhone. The AR application will search and suggest grocery items that correspond to the user's personalized plan, based on the location data and the inventory known for that particular grocery store. The user can also have particular advertisements targeted to them based not only their personalized plan, but specifically targeted based on contextual data gathered by the AR application.

Next, once the image is received, the method can include a process of evaluating the image, video stream, or contextual data for target food or beverage content. This target food or beverage content can include any of a restaurant menu, ingredient list, beverage, food product, grocery item, supplement, medication or food label by performing a step 704 of determining ingredients, substances and nutritional components of the target food or beverage content followed by a step 706 of determining attributes of the items that are indicative of nutritional values. These attributes include likely items in a dish or product and their corresponding nutritional and program adherence values.

In general, target food or beverage content includes any object having nutritional items that can be searched or evaluated based on their attributes. For example, an item on a menu comprises ingredients that each have nutritional data associated therewith. As noted above, example of the target food or beverage content includes, but is not limited to a restaurant menu, ingredient list, beverage, food product, grocery item, supplement, medication or food label, or other similar items known to one of ordinary skill in the art with the present disclosure before them.

In some embodiments, the method includes a step 708 of comparing the attributes to a personalized plan established for a user. That is, what is discovered on the menu through deep learning or artificial intelligence evaluation of the menu is compared to the personalized plan established for the user. Specific details on generating personal plans for users are described in greater detail supra.

Next, the method includes a step 710 of generating an augmented reality overlay for the target food or beverage content that comprises any of icons, text, numbers, graphs in order to highlight or obscure items on the target food or beverage content that do not comply with the personalized plan established for the user.

In some embodiments, the methods can include generating and displaying on the augmented reality overlay a dynamic adherence score for any of the items on the menu, food product or food label. This is illustrated in FIG. 3, for example. Other example overlays are in FIGS. 8A-B. As noted above, the dynamic adherence score is indicative of how well the item adheres to the personalized plan established by considering for the item any of required time lapse, periodicity, quantity, sequence, food and activity logs, sensors, external data sources, user context, and combinations thereof.

In some embodiments, the method can include receiving biometric or user-generated feedback after the user image of the menu, food product or food label. For example, data is collected after a user eats the items selected. Biometric feedback or a survey could be completed that would provide empirical data about what the user experienced as a function of eating the item. Some embodiments allow for updating the personalized plan established for the user based on the feedback.

In some instances, the biometric or user-generated feedback comprises any of relations and specific sequences of foods, activities, symptoms, and outcomes. That is, the consumption of the menu item is not considered in isolation, but in context and in multi-faceted review.

In some embodiments, the method can also include matching the image or video of the restaurant menu, ingredient list, beverage, food product, grocery item, supplement, medication or food label to a source image, markers, and/or data in a database. This data can include categorized and AR enabled content in the database, which includes, but is not limited to nutritional information or other previously generated AR content that matches what is determined to be included in the target food or beverage content.

The source image is created from a restaurant menu, ingredient list, beverage, food product, grocery item, supplement, medication or food label that is performed prior to the utilization of the augmented reality. The method can include the system using the source image in the database when a match is found. In this instance, the source image has been converted into an augmented reality enabled item. In essence, the image, video stream or contextual data viewed by the user through their device is matched to an AR version of the same image stored in a database.

Some embodiments include receiving a request for a recommendations stored in the database. It will be understood that the recommendations comprise at least one item that adheres to the personalized plan established for the user. Next the recommendations are displayed using the augmented reality application. As noted above, the method can also include calculating and displaying an adherence score that is indicative of how well the least one item that adheres to the personalized plan established for the user.

In some embodiments, the conversion of the source image into the augmented reality enabled image relies on a multi-model, multi-ontology, multi-label deep neural network (mLOM). The mLOM is used to generate a list of ingredients, substances and nutrients for each item by using a plurality of models, with each of the plurality of models predicting within a specific domain. In some instances, each ontology is comprised of a plurality of labels associated with the attributes of the items that are indicative of nutritional values.

With respect to the personalization aspects, the method includes obtaining input from a multivariate causation system that comprises empirical lifestyle programs, dietary plans, nutrition plans, and lifestyle programs, dietary plans, nutrition plans, and empirical evidence-based programs and selecting a dietary program for the user that is based on the input from the multivariate causation system and information of the user comprising genetics, biomarkers, profile, activities, background, clinical data, and combinations thereof.

This process can also include converting the lifestyle programs, dietary plans, nutrition plans, and empirical evidence-based programs into rule sets. In one embodiment a ruleset stack is created from a plurality of distinct dietary restrictions included in the lifestyle programs, dietary plans, nutrition plans, and empirical evidence-based programs, wherein the ruleset stack is further configured based on any of goals, biometrics, biomarkers, genetics, demographics, lifestyle and combinations thereof.

In one or more embodiments, at least a portion of the lifestyle programs, dietary plans, nutrition plans, and empirical evidence-based programs selected for use are obtained from the database based on a comparison of the user to a plurality of other users with respect to any of goals, biometrics, biomarkers, genetics, demographics, lifestyle and combinations thereof.

In various embodiments, the method includes updating the personalized plan using empirical feedback gathered from the user or from biometric measuring devices utilized by the user. The empirical feedback is processed using a low entropy causation function.

FIGS. 8A-B illustrate additional views of an AR overlay of an image obtained on a mobile device that executes an application of the present disclosure. In FIG. 8A, a mobile device 800 configured to perform the AR overlay methods described herein is illustrated as providing an overlay on a menu 802 (target food or beverage content). A selectable item 804 is displayed with a color such as green, indicating that the item has an adherence score that is acceptable based on the user's personalized plan. Each overlay of an item can be augmented with additional information. For example, an icon 806 if selected can provide the user with additional information about the selected item. This could include a warning, the adherence score, information about the item such as nutritional facts, and so forth.

FIG. 8B illustrates additional views of an AR overlay 810 of an image obtained on a mobile device that executes an application of the present disclosure. In this instance, the device is being used to view an item (target food or beverage content) on a grocery store shelf. An overlay can include information such as an adherence score 812 or other indicative information about the product such as price or nutritional information.

Some embodiments of the present disclosure provide for the of a Decision Augmentation Token (DAT) Blockchain Technology. The DAT blockchain technology is used to create the conditions for individuals to monetize their future long-term health by proving adherence to a lifestyle and by contributing certified data streams that can be used to further enhance the decision-making process for other communities and community members.

For example, the healthier choices a person makes, the less healthcare costs in the future, and the more productive the person can be. Therefore, the more that person will be saving money and contributing to their community and to society at large. Individuals, and those who guide and support their decision-making process toward health, longevity and productivity, should benefit from the long-term value they are creating.

The decision augmentation token blockchain technology sets an incentive economy to allow the stakeholders to recommend and make the right sequence of lifestyle choices towards long-term outcomes.

Decision Augmentation Stakeholders

Decision Augmentation Communities

Communities are created by persons or entities that define a set of lifestyle rulesets (e.g. dietary plans such as paleo, vegan, Mediterranean, as well as those with additional protocols e.g. '5+2 intermittent fasting') towards specific user-defined goals (e.g. longevity, health optimization, chronic disease prevention or diabetes reversal).

The rulesets are initially based on peer-reviewed evidence-based publications, and subsequently evolve by using the multivariate causation technology to fine-tune and enhance the rulesets.

These rulesets are intended to help individual members that join their communities to enhance their decision-making process towards their set goal(s).

Each community will have a creator that can be an individual, group of individuals, an institution or a corporation.

The community creator will prime the system with (a) the lifestyle rulesets, (b) the expected outcomes, (c) the progress vesting events, (d) the types of certifications that it will require for each data point, and (e) the distribution percentages of decision augmentation tokens amongst the different stakeholders (members, community, influencers and certifiers).

The more certified and high quality data points and data sequences the community contributes and uploads to the blockchain, the more probabilities it has of "farming" decision augmentation tokens.

Each community will be measured based on their "vesting success" measured as the collective certified progress towards stated outcomes.

The distribution percentages amongst stakeholders for the decision augmentation tokens will also be published along with the expected vested token earnings for an average successful member.

Published parameters and metrics will allow existing and potential new members to know the efficacy of the lifestyle towards their expected goals and their expected token earnings. These measures of success towards the different member goals will be published and be extractable from the blockchain.

Decision Augmentation Community Members

Individual members select and join a community that shares their goal/s and that provide decision augmentation. Receive a part of the decision augmentation tokens from their community earnings based on their individual data contributions as both community members, as well as influencers where applicable. Vest their decision augmentation tokens as they prove adherence to the lifestyle ruleset and achieve certified progress towards the goal.

Decision Augmentation Influencers

Influencers are the individuals, entities or machine algorithms that provided the most significant contribution towards the selection of each suggested option. Each community will have a main influencer that will receive a percentage of all the tokens awarded every time the lifestyle rulesets are followed and the set goals are met. In most cases the influencer is the community creator, but if the member chooses to follow the advice of a fellow community member that decision will then attributed to that fellow member as an influencer. For example, a member can be following a vegan diet from a renowned author to reverse her heart disease, but when she arrives at a restaurant she may choose to follow the advice from another vegan about a good menu item they have recommended. In this example the influencer for that particular decision would have been her fellow vegan, instead of the author. Influence can also be distributed to those members that have "walked the path" before and have achieved the expected outcomes. The result of using the multivariate causation technology to generate sequences of choices is that it extracts these sequences from these pioneering community members. Therefore, these users will be influencing the choices of future members and would receive a part of the influencer DATs depending on the configuration of each community.

Influence is not only measured in relation to the choices presented, but also in the when and how these options are presented. There can be a second level of influence which is how an option is presented, (for example the wording, images, color, etc.), along with the when it is presented (as a proactive nudge) can completely change the effectiveness of getting individual members to make the right choice.

Decision Augmentation Certifiers

Certifiers are the individuals, entities, or machine algorithms that certify the choices made, data streams or progress towards an outcome that a community member is posting to the blockchain.

For example a DAT certifier can be a laboratory testing company that certifies blood test results, a supermarket proving adherence to the recommended food/s with purchases or a device that monitors and reports my activity and sleep patterns.

Decision Augmentation Tokens (DAT)

DATs are earned periodically by communities in a semi-random way through a proof-of-stake algorithm. The proof-of-stake algorithm considers the amount of data and the quality of the certifications that each community has contributed to the blockchain and the amount of time since they last received DATs to weigh into the random allocation of new DATs.

Once DATs are assigned to a community, the entirety of these tokens are simultaneously distributed to community members, certifiers and influencers based on the block-chain evidence.

These DATs are first received as unvested tokens that cannot be sold, transferred or traded until they are vested. Vesting happens by submitting evidence that confirms progress towards the stated goal.

Fully vested DATs can be exchanged, sold and purchased by the stakeholder who earned them, whereas non-vested tokens cannot be exchanged and are accounted for at the community level.

Fully vested tokens may be available for purchase through an initial token offering to help finance and kickstart the token economy.

Decision Augmentation Token Economy

The incentives are set so that: (a) long-term second and third order outcomes (like health, longevity or productivity) are prioritized over short-term first-order decisions (like avoiding the pain of exercise or over-indulging on carbs to create a dopamine rush). To achieve a long-term incentive, we are implementing the vesting of the tokens over a period of time upon uploading certified periodical progress or the achievement of the stated expected outcome; (b) the more valuable information streams each community or individual contribute, the more DATs they can potentially receive; (c) the more that each community or individual can prove progress towards their stated goals, the more DATs that they can vest; and/or (d) the distribution of the DATs is split amongst the different stakeholders that participated in making the right series of choices that have led to the desired outcomes. Each individual community member, upon making each correct decision earns DATs, and those DATs are split along with the DA influencer, the DA certifier and in some cases with the rest of their community.

Communities can also choose to have fiat money reserves to distribute amongst their community members with the same rules as the farmed tokens. A use of this would be to create and manage "cost sharing" communities where members save money together towards future healthcare or health prevention costs. Those reserves can be used to pay for member medical or prevention bills based on their claims. Each claim then becomes part of the evidence towards (or against) the stated goals. Therefore the money left over that was not used for paying claims can be used to purchase fully vested tokens, redistributed and allocated to those members who have been following the lifestyle ruleset and that have had the desired outcomes.

Decision Augmentation Blockchain

Blockchain storage of the sequence of certified decision events and proof of progress towards expected outcomes. Blockchain keeps track of effectiveness and efficiency of each individual, influencer and community by measuring token vesting. Blockchain keeps track of when and how options were presented.

Figure 9:
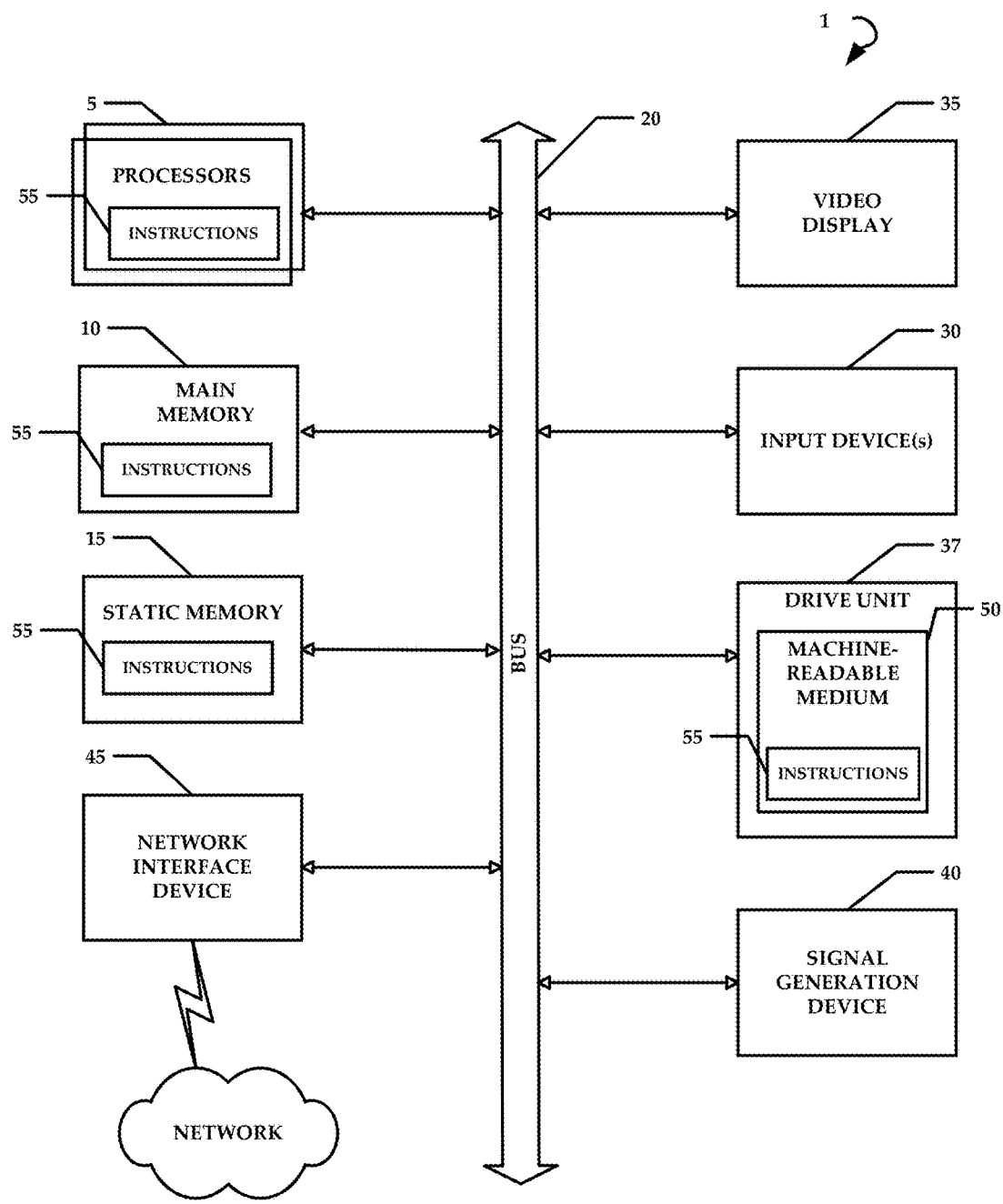
FIG. 9 is a diagrammatic representation of an example machine in the form of a computer system.
Figure 10A:
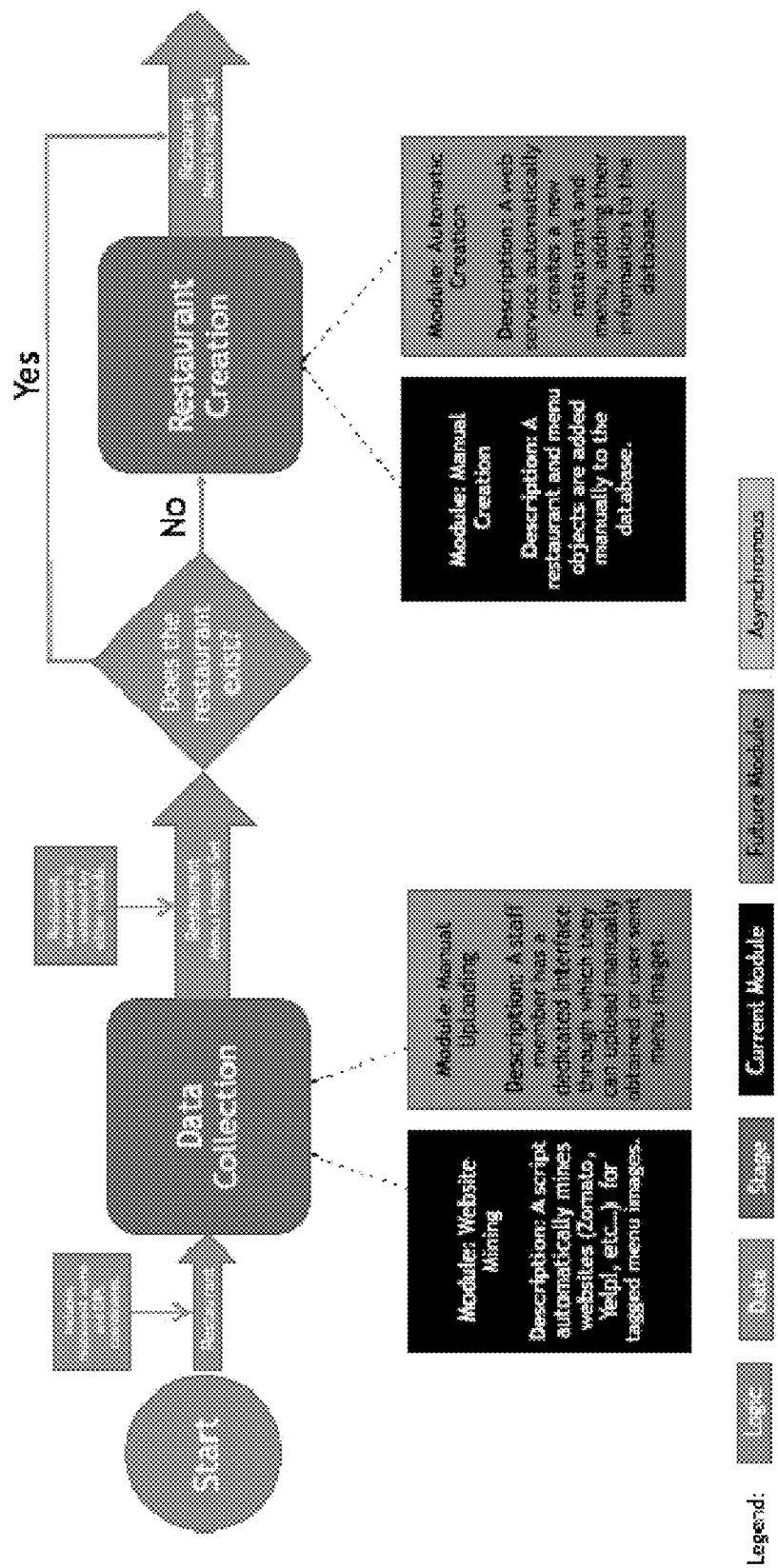
FIGS. 10A-D collectively illustrate an example flow diagram of an augmented reality data creation pipeline.
Figure 10B:
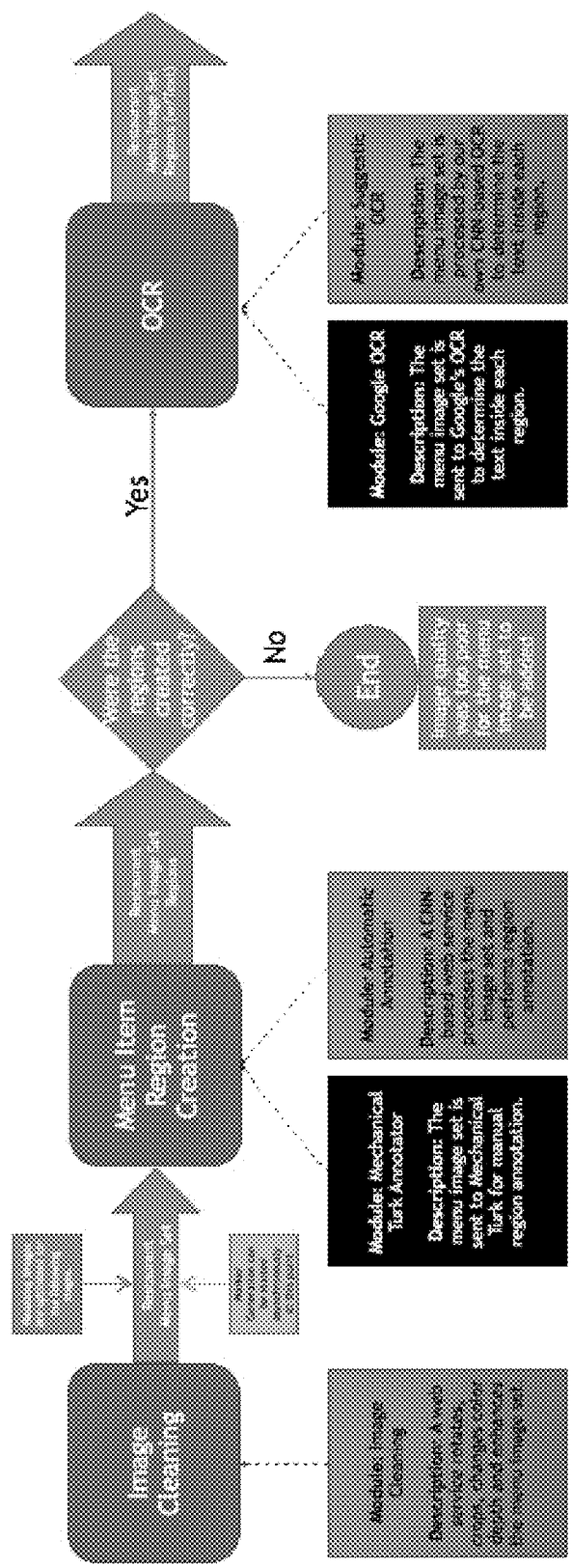
Figure 10C:
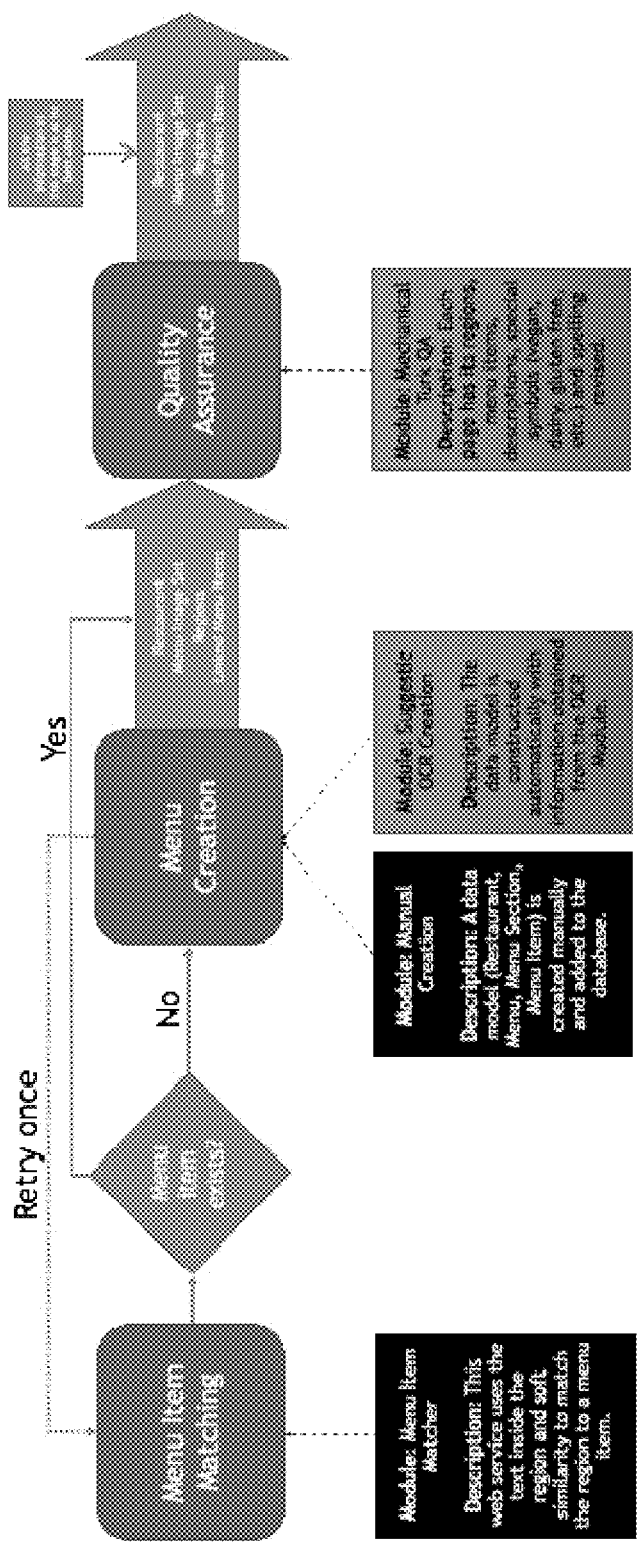
Figure 10D:
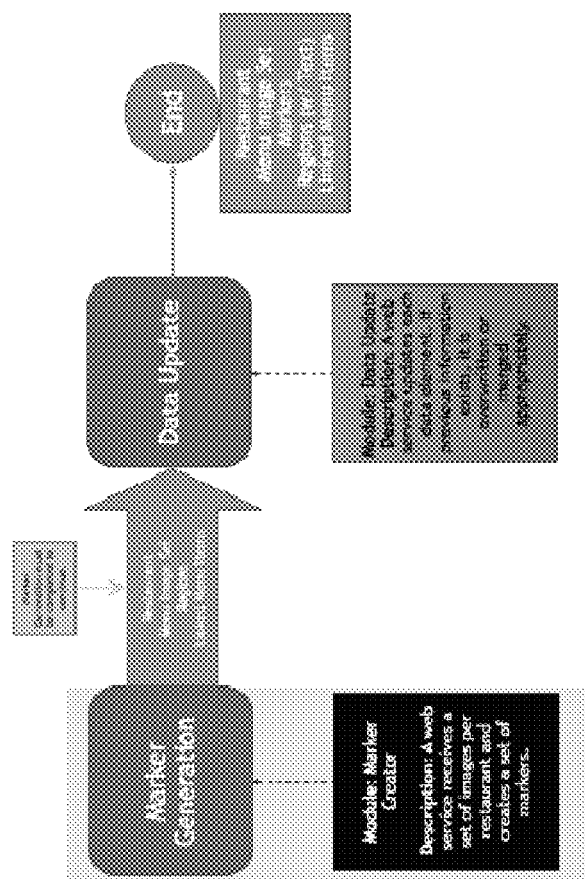

FIG. 9 is a diagrammatic representation of an example machine in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a portable music player (e.g., a portable hard drive audio device such as a Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1 includes a processor or multiple processor(s) 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alpha-numeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The disk drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processor(s) 5 during execution thereof by the computer system 1. The main memory 10 and the processor(s) 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated.

The terminology used herein is for the purpose of describing particular embodiments only and is not intended to be limiting of the technology. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that like or analogous elements and/or components, referred to herein, may be identified throughout the drawings with like reference characters. It will be further understood that several of the figures are merely schematic representations of the present technology. As such, some of the components may have been distorted from their actual scale for pictorial clarity.

The flowchart and block diagrams in the Figures illustrate the architecture, functionality, and operation of possible implementations of systems, methods and computer program products according to various embodiments of the present technology. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It is noted at the outset that the terms "coupled," "connected", "connecting," "electrically connected," etc., are used interchangeably herein to generally refer to the condition of being electrically/electronically connected. Similarly, a first entity is considered to be in "communication" with a second entity (or entities) when the first entity electrically sends and/or receives (whether through wireline or wireless means) information signals (whether containing data information or non-data/control information) to the second entity regardless of the type (analog or digital) of those signals. It is further noted that various figures (including component diagrams) shown and discussed herein are for illustrative purpose only, and are not drawn to scale.

While specific embodiments of, and examples for, the system are described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel, or may be performed at different times.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A method, comprising:
    receiving any of an image, a video stream, and contextual data from a mobile device;
    evaluating any of the image, the video stream, and the contextual data for target food or beverage content by:
        determining ingredient and nutritional components of the target food or beverage content; and
        applying an augmented reality overlay to the target food or beverage content based on the ingredient and nutritional components;
    wherein a personalized plan is generated by: obtaining input from empirical evidence-based lifestyle and nutritional programs; and
    selecting a dietary program for the user that is based on information comprising genetics, biomarkers, profile, activities, background, clinical data, and combinations thereof;
    converting lifestyle programs, dietary plans, nutrition plans, and empirical evidence-based programs into rule sets; and
    creating a ruleset stack by merging a plurality of any of lifestyle programs, dietary plans, nutrition plans, and empirical evidence-based programs, wherein the ruleset stack is further configured based on any of goals, biometrics, biomarkers, genetics, demographics, lifestyle and combinations thereof.

2. The method according to claim 1, wherein the target food or beverage content comprises any of restaurant menus, ingredient lists, beverages, food products, groceries, supplements, medications, food labels, and combinations thereof.

3. The method according to claim 2, further comprising generating a dynamic adherence score for any of the target food or beverage content wherein the dynamic adherence score is indicative of how well an item adheres to the personalized plan established by considering for the item any of required time lapse, periodicity, quantity, sequence, food and activity logs, sensors, external data sources, user context, and combinations thereof.

4. The method according to claim 3, wherein the augmented reality overlay comprises any of an icon, text, a number applied proximately to, or over, a portion of the target food or beverage content so as to highlight or obscure items included in the target food or beverage content that do or do not comply with the personalized plan established for the user.

5. The method according to claim 1, further comprising:
    receiving biometric or user-generated feedback; and
    updating the personalized plan established for the user based on the feedback.

6. The method according to claim 5, wherein the biometric or user-generated feedback comprises any of relations and specific sequences of foods, activities, symptoms, and outcomes.

7. The method according to claim 1, further comprising matching the image, video stream or contextual data to markers and data in a database, wherein the image or the video stream captures any of a restaurant menu, an ingredient list, a beverage, a food product, a grocery item, a supplement, a medication or a food label and data in the database when a match is found, wherein the image or the video stream is converted into an augmented reality enabled item or image.

8. The method according to claim 6, further comprising:
    receiving a request for any of a recommended image, markers, and data options overlay; and
    calculating and displaying an adherence score that is indicative of how well at least one item adheres to the personalized plan established for the user.

9. The method according to claim 6, further comprising converting the image or video stream into an augmented reality enabled image process pipeline that allows for any of image correction, marker creation, and links for each element to the ingredient and nutritional components using a multi-model, multi-ontology, multi-label deep neural network (mLOM).

10. The method according to claim 9, wherein the mLOM is used to generate specific ingredient, substance and nutritional components of items in the target food or beverage content that are indicative of nutritional values.

11. The method according to claim 1, further comprising prioritizing rulesets in the ruleset stack according to medical needs.

12. The method according to claim 1, wherein at least a portion of the lifestyle programs, dietary plans, nutrition plans, and empirical evidence-based programs selected for use are obtained from a database based on a comparison of the user to a plurality of other users with respect to any of goals, biometrics, biomarkers, genetics, demographics, lifestyle and combinations thereof.

13. The method according to claim 1, further comprising updating the personalized plan using empirical feedback gathered from the user or from biometric measuring devices.

14. The method according to claim 13, wherein the empirical feedback is processed using multivariate causation discovery to find patterns and sequences that best predict one or more desired outcomes, lab test results, environment and personal information based on one or more selected rulesets.

15. The method according to claim 14, further comprising generating a merged program or dietary plan for the user or a group of users based on multiple applied rulesets for the user or the group of users that also have individual ruleset based programs.

16. The method according to claim 15, wherein the personalized plan is updated using updated rulesets, empirical feedback, and active and passive feedback obtained from biometric feedback devices utilized by the user.

\* \* \* \* \*